(12) United States Patent
Chatterjee et al.

(10) Patent No.: US 10,729,082 B2
(45) Date of Patent: Aug. 4, 2020

(54) PAPAYA WITH NOVEL TRAITS AND METHODS FOR PRODUCING SUCH PAPAYA PLANTS

(71) Applicants: BENCHBIO PVT. LTD, Valvada (IN); NAMDHARI SEEDS PVT. LTD, Bangalore (IN); HORTIGENETICS RESEARCH (S.E. ASIA) LTD., Chiang Mai (TH)

(72) Inventors: Manash Chatterjee, Cambridge (GB); Anish Kumar Pullanchyottu Kizhakkeveettil, Kannur (IN); Anand Narasimhan, Bangalore (IN); Krishna Katta Ashwathaiah, Bangalore (IN); Darush Struss, Chiang Mai (TH); Conrado H. Balatero, Lipa (PH)

(73) Assignees: BENCHBIO PVT. LTD., Gujarat (IN); NAMDHARI PVT. LTD, Karnataka (IN); HORTINGENETICS RESEARCH (S.E. ASIA) LTD., Chiang Mai (TH)

( * ) Notice: Subject to any disclaimer, the term of this patent is extended or adjusted under 35 U.S.C. 154(b) by 88 days.

(21) Appl. No.: 15/785,051

(22) Filed: Oct. 16, 2017

(65) Prior Publication Data
US 2019/0110418 A1    Apr. 18, 2019

(51) Int. Cl.
A01H 5/08       (2018.01)
A01H 1/06       (2006.01)
C12N 15/01      (2006.01)
A01H 6/00       (2018.01)
A01H 1/04       (2006.01)
C12N 15/10      (2006.01)
C07K 14/415     (2006.01)

(52) U.S. Cl.
CPC ............... *A01H 5/08* (2013.01); *A01H 1/04* (2013.01); *A01H 1/06* (2013.01); *A01H 6/00* (2018.05); *C12N 15/01* (2013.01); *C07K 14/415* (2013.01); *C12N 15/102* (2013.01); *C12Q 2600/156* (2013.01)

(58) Field of Classification Search
None
See application file for complete search history.

(56) References Cited

U.S. PATENT DOCUMENTS 7,919,677 B2 *  4/2011  Caranta ............... C07K 14/415
                                                     435/5

OTHER PUBLICATIONS

Gonsalves, Annu Rev Phytopathol 36: 415-437, 1998 (Year: 1998).*

* cited by examiner

*Primary Examiner* — Elizabeth F McElwain
(74) *Attorney, Agent, or Firm* — IP Pundit LLC

(57) ABSTRACT

The present application relates to *papaya* plants having increased resistance to the *papaya* ringspot virus as compared to a wild type plant due to a mutation in the eukaryotic translation initiation factor 4e and/or eukaryotic translation initiation factor iso4e gene leading to non-functional eukaryotic translation initiation factor 4e and/or eukaryotic translation initiation factor iso4e proteins. Methods of producing such *papaya* plants having increased resistance to the *papaya* ringspot virus are described.

5 Claims, 2 Drawing Sheets
Specification includes a Sequence Listing.

PAPAYA WITH NOVEL TRAITS AND METHODS FOR PRODUCING SUCH PAPAYA PLANTS

TECHNICAL FIELD

The present invention relates to novel traits in *papaya* plants showing an increased resistance to *papaya* ringspot virus (PRSV) infection as compared to wild type *papaya*. The present invention also presents methods of generating such *papaya* plants using novel methods.

BACKGROUND

*Papaya* (*Carica papaya* L.) is a soft-wooded herbaceous dicotyledonous plant that belongs to the family Caricacea. The family Caricaceae, contains thirty five latex containing species spread over six genera i.e. *Carica* (1 species), *Cylicomorpha* (2 species), *Jarilla* (3 species), *Jacaratia* (7 species), *Horovitzia* (1 species) and *Vasconcellea* (21 species) (Fuentes and Santamaria, 2014). Only the genera *Carica*; is used as a fruit tree and, now-a-days, also as a nutraceutical and medicinal plant (O'Hare and Williams, 2014). *Papaya* originated from Southern Mexico and Central America (Fuentes and Santamaria, 2014) and spread throughout the world. *Papaya* has nine pairs of chromosomes (2n=18) and approximately 372 MB genome size (Ming et al., 2008). *Papaya* ranks first among fruits consumed (Hui et al., 2001), and also ranks first in nutritional profile (Bari et al, 2006; Ming et al., 2008; Manshardt, 1992). The main five countries that have been producing *papaya* for the last 50 years are India, Nigeria, Brazil, Mexico and Indonesia (Kumar et al 2014).

The *papaya* ringspot virus ("PRSV") is a member of the potyvirus group of plant viruses, which are pathogenic to several crop plants and is the most destructive disease in *papaya*. The name of the virus is taken from the ringed spots that form on the fruits of infected trees. Trees infected with PRSV develop symptoms such as mosaic and chlorosis of leaf lamina, water-soaked oily streaks on the petiole and upper part of the trunk, severe distortion of young leaves and formation of ring shaped spots on the fruits. If infected at seedling stage or within two months after planting, the tree might not bear any fruit leading to 100% losses. There are no wild species of *papaya* that show resistance to PRSV that can be used in breeding. Therefore, it is becoming more essential for plant breeders to develop plants that are resistant to infection from viruses, for example those from the Potyviridae family.

PRSV is transmitted by numerous species of aphids in a non-persistent manner to a limited host range of cucurbits and *papaya*. Currently the known solution for limiting loss to PRSV is by chemical control of vectors which is costly and does not provide 100% protection. The other solution is inducing resistance via transgenic route which is not only expensive but also not acceptable to consumers. Various attempts have been made to control or prevent infection of crops by PRSV, but these have met with limited success. U.S. Pat. No. 7,078,586 B2 (Gonsalves et. al 2006) describes a transgenic method of inducing resistance to the virus. This method involves the expression of nucleic acid sequences encoding coat protein of the mild mutant PRSV strain in transgenic *papaya* plants 'Sunup' which helps protect against infection of the PRSV to Hawaiin strains. However, the transgenic plants do not show resistance to PRSV strains outside Hawaii, such as Thailand and Jamaica PRSV strains (Gonsalves 2014). The variety 'Sunup' is a transgenic *papaya* ringspot virus resistant fruit crop which is currently grown in Hawaii, USA. In 2008, Ming et. al. first sequenced the *papaya* genome of the variety 'Sunup', having 3× genome coverage (Ming et al., 2008, Rachel, 2008). The *papaya* genome is reported to have about 13311 candidate genes (Ming et al., 2008) because of lack of gene duplications, which is quite different from other plant species. The genome is about three times the size of model plant *Arabidopsis thaliana* in terms of genome size, and contains far less number of disease resistance genes (Ming et al., 2008). It is possible that the genes in *papaya* might be involved in more than one function, as the estimated number of genes is quite low, compared to other species. Moreover, the *papaya* genome is highly euchromatic (Ming et al., 2008). Siar et al (2011), describe the production of PRSV resistant plants by backcrossing (BC) *papaya* plants following intergeneric hybridization between *C. papaya* and a *Vasconcellea quercifolia* with great difficulties. One PRSV-P resistant plant was produced after 114,839 seeds were dissected from 940 fruits of a back cross1 generation $BC_1$). The above breeding methods have their own drawbacks, such as constant efforts to produce large number of plants after crossing for screening and efficient embryo culture requirements which are not easy to undertake. Moreover at present most markets are reluctant to accept and consume genetically modified fruits. Furthermore, the cost of de-regulating these transgenic *papaya* seeds can be very high. At present, there are no natural PRSV resistant *Carica papaya* species in the world that can be crossed easily (Gonsalves, 2014). Since, the genome of *papaya* has been already sequenced, specific gene related information is available by performing intensive data mining and comparative analysis with other sequenced crops. The inventors have developed novel methods to produce non-transgenic PRSV resistant *papaya* plants by inducing mutations in the *papaya* genome and screening of desirable mutants using Allele Detection Platform (ADP) a variant of the TILLING (Targeting Induced Local Lesions IN Genomes) method (Kumar. et al, 2014)

TILLING offers an alternative way to manipulate endogenous genes for the improvement of crops without transgenic method. TILLING is a reverse genetics technique that uses traditional chemical mutagenesis to create libraries of mutagenized individuals that are later subjected to sensitive molecular screenings to discover induced mutations in genes whose sequence is known. By means of TILLING new allelic variants of the gene of interest can be identified hence new genotypes with potentially high agronomic value can be isolated and directly transferred for commercialization after backcrossing to the parent line. Using this technique potyvirus resistant lines in various crops have been developed in crops such as in melons, tomato etc., as described by Robaglia and Caranta (2006), Neito et al (2006) Neito et al (2007), Ruffel et al (2002), Nicaise et al (2003) Gao et al, (2004) Kang et al (2005), Ruffel et al (2005) Piron et al (2010). For example, Piron et al (2010) teaches the use of TILLING to induce potyvirus resistance to Potato Virus Y (PVY) and Pepper Mottle Virus (PepMoV) in tomatoes. Very recently, Pyott et al (2016), utilized CRISPR-Cas9 technology to introduce sequence-specific deleterious point mutations at the eIF(iso)4e locus in *Arabidopsis thaliana* to successfully engineer complete resistance to Turnip mosaic virus (TuMV), a major pathogen in field-grown vegetable crops. However, up until now, these methods have not been used to induce mutations in *papaya* plants to develop PRSV resistant plants.

Therefore, embodiments of the present invention may ameliorate one or more of the above-mentioned problems:

Embodiments of the present invention may provide a *papaya* plant having increased resistance as compared to wild type *papaya* plants to the *papaya* ringspot virus due to a mutation in the eIF4e and/or eIF(iso)4e gene.

Another, embodiment of the present invention may provide a *papaya* plant having increased resistance as compared to the wild type *papaya* plant to the *papaya* ringspot virus due to a mutation in the eIF4e and/or eIF(iso)4e gene leading to non-functional eIF4e and/or eIF(iso)4E protein.

Another embodiment of the present invention may provide food and food products incorporating *papaya* fruits derived from a *papaya* plant having an increased resistance to the *papaya* ringspot virus caused by a mutation in the eIF4e and/or eIF(iso)4e gene and non-functional eIF4e and/or eIF(iso)4e proteins.

Yet another embodiment of the present invention may provide, a *papaya* plant having increased resistance to *papaya* ringspot virus created by the steps of obtaining plant material from a parent *papaya* plant, inducing at least one mutation in at least one copy of a eIF4e and/or eIF(iso)4e gene of the plant material by treating the plant material with a mutagen to create mutagenized plant material, culturing and growing the mutagenized plant material to produce progeny *papaya* plants, isolating DNA or RNA from progeny *papaya* plants and analyzing progeny *papaya* plants to detect at least one mutation in at least one copy of a eIF4e and/or eIF(iso)4e gene, leading to loss of function of the eIF4e and/or eIF(iso)4e protein and selecting progeny *papaya* plants and phenotyping plants that possess increased resistance to *papaya* ringspot virus; and repeating the cycle of culturing the progeny *papaya* plants to produce additional plants with increased resistance to *papaya* ringspot virus when compared to wild type *papaya* plants.

Some or all these and other objects of the invention can be achieved by way of the invention described here-in after.

SUMMARY OF THE INVENTION

Thus, an aspect of the present invention provides a *papaya* plant having increased resistance to the *papaya* ringspot virus as compared to a wild type plant due to a mutation in the eIF4e and/or eIF(iso)4e gene leading to non-functional eIF4e and/or eIF(iso)4e proteins.

Another aspect of the present invention may provide methods of producing *papaya* plant with increased resistance to *papaya* ringspot virus created by the steps comprising:
 a. treating *papaya* seeds with a mutagen and growing such plants;
 b. extracting DNA and/or RNA and analyzing progeny *papaya* plants to detect at least one mutation in at least one copy of a eIF4e and/or eIF(iso)4e gene/RNA transcript leading to non-functional eIF4e and/or eIF(iso)4e proteins;
 c. selecting progeny *papaya* plants carrying the mutation and that have increased resistance to *papaya* ringspot virus phenotypically;
 d. selecting directly for increased disease resistance by growing the progeny *papaya* plants in the presence of the disease.
 e. repeating the cycle of growing and culturing the progeny *papaya* plants to produce additional plants with increased resistance to *papaya* ringspot virus; and
 f. combining two lines both homozygous for the mutation in eIF4e gene present in the two parents to generate a hybrid; or combining the homozygous mutants in eIF(iso)4e gene present in the two parents to generate a hybrid; or combining the homozygous mutants in eIF4e and/or eIF(iso)4e genes present in two different parent plants to generate a hybrid by gene stacking.

Another aspect of the present invention may provide food and food products incorporating *papaya* fruits with increased resistance to the *papaya* ringspot virus as compared to wild type *papaya* plant caused by a mutation in the eIF4e and/or eIF(iso)4e gene leading to non-functional eIF4e and/or eIF(iso)4e proteins.

BRIEF DESCRIPTION OF SEQUENCES

Figure 1:
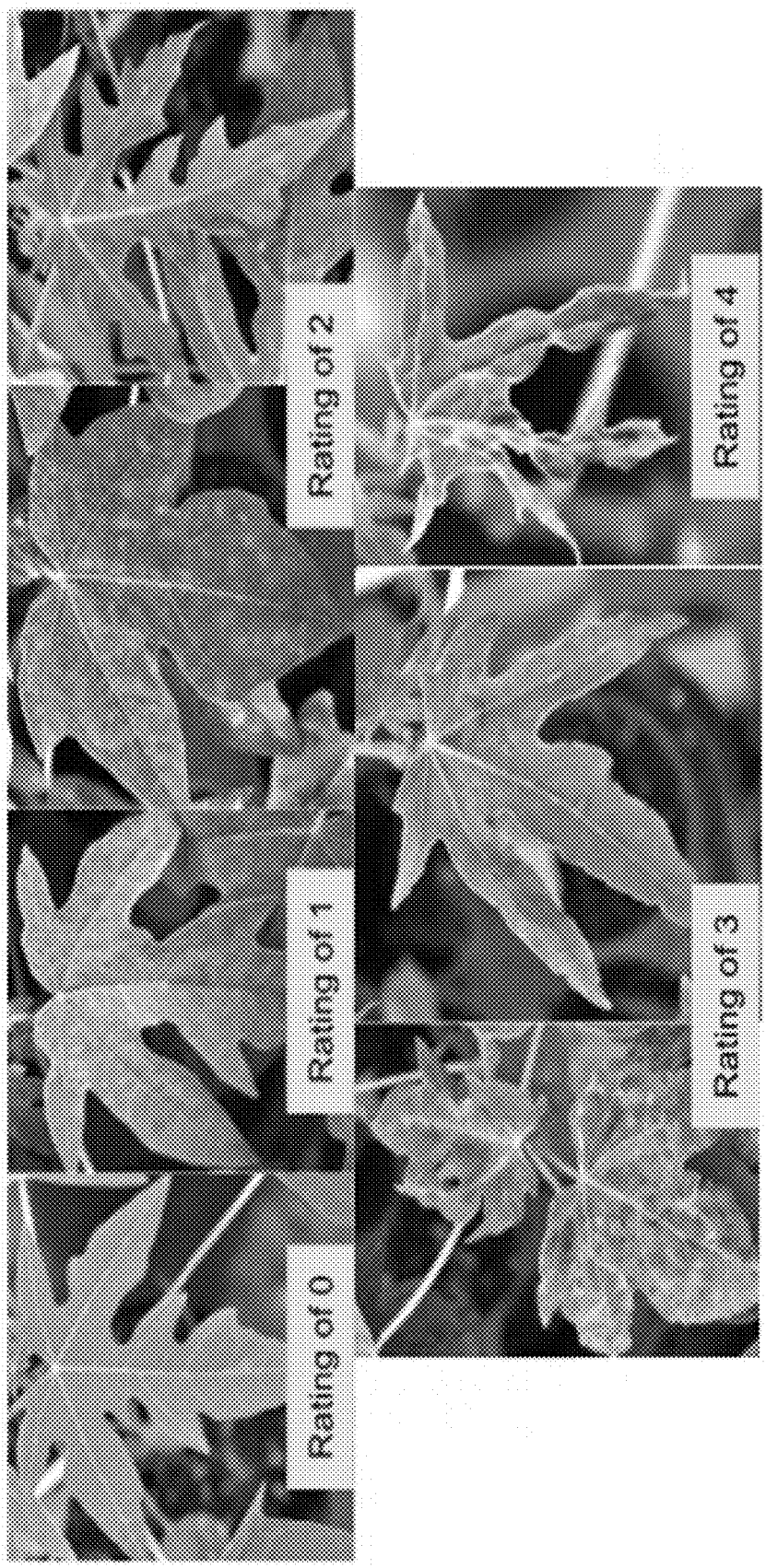
FIG. 1 shows disease severity rating scale of *papaya* ringspot virus infection.

SEQ ID NO: 1 pertains to wild type eIF4e gene nucleotide sequence in *papaya* (Annotated from sequencing report and NCBI sequence: ABIM01000000, ABIM01005433.1, LG8 contig 5440);

SEQ ID NO: 2 pertains to mutated eIF4e nucleotide sequence in *papaya* (*papaya* mutant line number, M2(0.3)-1709 G2112A (UGG->UGA) W140*);

SEQ ID NO: 3 pertains to mutated eIF4e nucleotide sequence in *papaya* (*papaya* mutant line number M2(0.3)-1220 G2301A (GGA->GAA) G173E);

SEQ ID NO: 4 pertains to wild type eIF4e gene (mRNA) sequence in *papaya* (GenBank: FJ644949.1);

SEQ ID NO: 5 pertains to mutated eIF4e gene (mRNA) sequence in *papaya* (*papaya* mutant line number M2(0.3)-1709);

SEQ ID NO: 6 pertains to wild type eIF4e amino acid sequence in *papaya* (protein_id="ACN38307.1");

SEQ ID NO: 7 pertains to mutated eIF4e amino acid sequence in *papaya* (*papaya* mutant line number M2(0.3)-1709);

SEQ ID NOs: 8, 10, 12, 14, 16, and 18 pertain to *papaya* eIF4e forward primer sequences;

SEQ ID NOs: 9, 11, 13, 15, 17, and 19 pertain to *papaya* eIF4e reverse primer sequences;

SEQ ID NO: 20 pertains to eIF(iso)4e gene nucleotide sequence in wild type *papaya* (gb|ABIM01010894.1|: 25000-29500, *Carica papaya* chromosome LG6 contig_10909, whole genome shotgun sequence);

SEQ ID NO: 21 pertains to eIF(iso)4e mutant nucleotide sequence in *papaya* (*papaya* mutant line number, M2(0.3)-552 G2046A (GGG->GAG) G105E);

SEQ ID NO: 22 pertains to wild type eIF(iso)4e gene (mRNA) sequence in *papaya* (GenBank: FJ595992.1);

SEQ ID NO: 23 pertains to mutated eIF(iso)4e gene (mRNA) sequence in *papaya* (*papaya* mutant line number M2(0.3)-552);

SEQ ID NO: 24 pertains to wild type eIF(iso)4e amino acid sequence in *papaya;*

SEQ ID NO: 25 pertains to mutated eIF(iso)4e amino acid sequence in *papaya* (*papaya* line number M2(0.3)-552);

SEQ ID NOs: 26-37 pertain to *papaya* eIF(iso)4e forward primer sequences; and

SEQ ID NOs: 38-49 pertain to *papaya* eIF(iso)4e reverse primer sequences.

DETAILED DESCRIPTION OF THE INVENTION

As used herein, the term "plant" includes the whole plant or any parts or derivatives thereof, such as plant organs (e.g., harvested or non-harvested fruits, flowers, leaves, stem, roots etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries, fruits flowers, leaves, seeds, tubers, clonally propagated plants, roots, stems, cotyledons, hypocotyls, root tips and the like. Also, any developmental stage is included, such as seedlings, immature and mature, etc.

An "M1 population" is a plurality of mutagenized seeds/plants of a certain plant line or cultivar. "M2, M3, M4, etc." refers to the consecutive generations obtained following selfing of a first mutagenized seed/plant (M1).

The term "selfing" means self-pollination, e.g., when the pollen self-pollinates the ovule of the same plant.

A "mutation" in a nucleic acid molecule coding for a protein is a change of one or more nucleotides compared to the wild type sequence, e.g. by replacement, deletion or insertion of one or more nucleotides. A "point mutation" is the replacement of a single nucleotide, or the insertion or deletion of a single nucleotide.

As used herein, "disease resistance" refers to the acquired (i.e. inherited) ability of a plant to survive (e.g. grow and optionally reproduce) and/or restrict the multiplication of the pathogen following exposure to a pathogen that can cause disease in wild type plants. In other words, the plant has phenotypically changed compared to the wild type plant such that it is less affected and lacks disease symptoms. In a plant, disease resistance may be naturally occurring or induced by such techniques as genetic engineering or selection of variants produced by tissue culture or mutagenesis. A "disease resistant" plant is therefore a plant that is resistant to disease at a level that would normally kill, or inhibit the normal growth of, a wild type plant of the same species. An "increased resistant" plant may be defined as a plant which when compared to wild type plant has an increased ability to survive (e.g. grow and optionally reproduce, lack disease symptoms) following exposure to a disease that would normally affect the wild type plant.

A "loss-of-function protein" refers to a mutant eIF4e or eIF(iso)4e protein that may be a truncated protein that will not encode a functional eukaryotic RNA translation initiation factor. "Non-functional and loss-of-function" may be used interchangeably.

The present invention may provide methods to generate *papaya* plants that have increased resistance as compared to the wild type *papaya* plant to *papaya* ringspot virus due to a mutation in at least one of its eIF4e and/or eIF(iso)4e genes, leading to non-functional proteins without the inclusion of foreign nucleic acids in the *papaya* genomes The present invention may also provide a series of independent mutations in the eIF4e and/or eIF(iso)4e gene; *papaya* plants having these mutations in at least one of its eIF4e and/or eIF(iso)4e genes; and a method of creating and identifying similar and/or additional mutations in the eIF4e and/or eIF(iso)4e gene of *papaya*.

The inventors in the present invention used a method called TILLING (Targeting Induced Local Lesions in Genomes) (McCallum et al., 2000; Till et al. 2003, Triques et al., 2007). TILLING, relies on random mutations in the genome caused by treatment of the seeds using chemical or physical mutagens which causes single nucleotide polymorphism mutations in the target genome. DNA or RNA from samples from the resulting mutagenized plants are pooled and subjected to screening for mutations in the gene of interest. Once a mutation is identified in the gene of interest, the seeds of the plant carrying that mutation are grown and genotyped for heterozygous and homozygous mutants using the gene marker. M2 plants from a selected family may then be subjected to artificial inoculation with the virus and ELISA test is performed to check for young plant resistance and also grown in hotspots (a place where the incidence of target disease infection is very high) to check for adult plant resistance. The M2 plants are further grown into adults and M3 seeds are harvested. The M3 plants are screened again in disease hotspots and screened for the disease resistance phenotypic characteristics associated with the gene of interest.

The single homozygous mutants in the eIF4e or eIF(iso)4e gene exhibiting a disease resistant phenotype may be combined with another homozygous eIF4e or eIF(iso)4e mutant line to generate a PRSV resistant hybrid *papaya* variety. The single gene eIF4e mutants may also be crossed with mutants in the eIF(iso)4e gene to generate a hybrid carrying resistance derived from combination of single mutants in eIF4e and eIF(iso)4e by stacking leading to resistance for a longer period "(durable resistance)".

Using the process of TILLING, the inventors in the present invention have induced independent mutations in the eIF4e and/or eIF(iso)4e genes in *papaya*, causing single nucleotide polymorphisms that resulted in non-functional proteins thereby leading to increased resistance to the *papaya* ringspot virus when compared to wild type *papaya* plant. The eIF4e gene encodes a eukaryotic RNA translation initiation factor. It is known that an isoform of eukaryotic translation initiation factor eIF4e from *Arabidopsis thaliana* interacts with the viral protein VPg of the Turnip Mosaic Virus (TuMV). Several natural resistance genes against potyviruses, from distinct crops, were shown to encode defective forms of eIF4e and eIF(iso)4e, for example, pvr2 for pepper resistance against Potato Virus Y (PVY), Tobacco Etch Virus (TEV), mol for resistance in lettuce to Lettuce Mosaic Virus (LMV), sbml for resistance in pea to Pea Seed-Borne Mosaic Virus (PSbMV) and pot-1 for resistance in tomato to Potato Virus Y (PVY) and Tobacco Etch Virus (TEV) (Caranta et al, 1996). Although these genes control diverse resistance phenotypes, resistance in all cases results from a small number of amino acid changes in the proteins encoded by the recessive resistance alleles that harbour point mutations. Melon Necrotic Spot Virus (MNSV) resistant melon plants have been generated by TILLING of the eIF4e gene in melon (Nieto et al., 2007). As PRSV is a potyvirus it is hypothesised that TILLING orthologs of *Papaya* eIF4e and eIF(iso)4e genes has a good potential of generating PRSV resistant lines. U.S. Pat. No. 919,677 B2 (CARANTA et al. 2004) demonstrated that there exists a co-relation between the eIF4e and VPg gene of the potyvirus and mutations in eIF4e results in resistance in Solanaceae, Cucurbitaceae, Cruciferae and Compositae plants. However, no prior art exists that demonstrates the use of this method for inducing potyvirus resistance in *papaya*.

Thus, an aspect of the present invention may provide, a *papaya* plant with increased disease resistance to *papaya* ring spot virus as compared to wild type *papaya* plant due to mutation(s) in at least one of its eIF4e and/or eIF(iso)4e genes.

Based on the type of mutation(s), the increase in disease resistance may be 60% as compared to wild type, the increase in disease resistance may be 70% as compared to wild type, the increase in disease resistance may be 80% as compared to wild type, the increase in disease resistance may be 90% as compared to wild type, the increase in disease resistance may be 100% as compared to wild type, the increase in disease resistance may range from 60%-100% as compared to wild type, the increase in disease resistance may range from 60%-90% as compared to wild type, the increase in disease resistance may range from 70%-100% as compared to wild type, the increase in disease resistance may range from 80%-100% as compared to wild type, the increase in disease resistance may range from 90%-100% as compared to wild type, the increase in disease resistance may range from 70%-90% as compared to wild type, the increase in disease resistance may range from 70%-80% as compared to wild type, the increase in disease resistance may range from 80%-90% as compared to wild type.

In an embodiment, the *papaya* plant may comprise plant organs (e.g., harvested or non-harvested fruits, flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries, fruits, (e.g., harvested tissues or organs, such as harvested *papaya* or parts thereof), flowers, leaves, seeds, tubers, clonally propagated plants, roots, stems, cotyledons, hypocotyls, root tips and the like. Also, any developmental stage is included, such as seedlings, immature and mature, etc.

In an embodiment, the mutation is induced using the mutagens that may be chemical or physical mutagens.

In an embodiment, the chemical mutagen used may be selected from but not limited to ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3(ethyl-2-chloro-ethyl)aminopropylamino]acridine dihydrochloride (ICR-1 70), and formaldehyde.

In an embodiment, the mutation is induced using physical mutagens such as fast neutrons or electromagnetic radiation such as X-rays or gamma rays.

In an embodiment, methods by which mutations like deletion and insertions may be induced may include but are not limited to new breeding techniques (NBTs) that include targeted gene editing using, TALEN, Zinc Finger Nucleases (ZFN), Oligonucleotide-directed mutagenesis (ODM) and CRISPR-Cas9. Gene editing techniques may be used to induce targeted mutations, insertions or deletions in the *papaya* genes eIF4e and/or eIF(iso)4e and other members of this gene family which are involved in the cascade of molecular mechanisms such as host protein-viral protein interaction which is required for PRSV genes replication within *papaya* cells leading to PRSV resistance in *papaya*.

Thus, in this embodiment, *papaya* seeds from various strains may be cleaned and treated using 1M KNO3 solution for improving the germination as per methods known in the art. After which the seeds may be washed and treated with a mutagen (M1 seed) such that the mutagen selected causes point mutations. The M1 seeds are then grown to maturity and M2 seeds are harvested individually from each plant. The M2 seeds are then sown and the plants may then be prepared for DNA extraction using any suitable method of plant DNA preparation to prepare the *papaya* plant DNA for eIF4e and/or eIF(iso)4e mutation screening such as using commercial DNA extraction kits following manufacturer's protocol, for example, QiagenDneasy plant mini kit or similar known DNA kits. *Papaya* M2 DNA samples may then be pooled to expedite screening for mutations in eIF4e and/or eIF(iso)4e gene from the entire population of M2 plant families originating from the mutagenized plant tissue. The size of the pooled group may depend on the sensitivity of the screening method used. In accordance with one aspect of an exemplary embodiment of the invention, groups of four or more individual *papaya* plants per M2 family are pooled.

In an embodiment, after the DNA samples are pooled, the pools are subjected to eIF4e and/or eIF(iso)4e sequence-specific amplification techniques, such as Polymerase Chain Reaction (PCR). Any primer specific to the eIF4e and/or eIF(iso)4e locus or the sequences immediately adjacent to the eIF4e and/or eIF(iso)4e locus may be utilized to amplify the eIF4e and/or eIF(iso)4e sequences within the pooled DNA sample. Preferably, the primer is designed to amplify the regions of the eIF4e and/or eIF(iso)4e locus where useful mutations are most likely to arise. Most preferably, the primer is designed to detect mutations in the coding region of the eIF4e and/or eIF(iso)4e gene. Preferably, the primer used may be such that it avoids known polymorphic sites to ease screening for point mutations. The present invention may therefore provide in an embodiment, suitable primers for this purpose (SEQ ID NOs: 8-19 and 26-49).

In an embodiment, DNA and/or RNA from the mutagenized *papaya* plant or subsequent generations may be sequenced by various sequencing methods such as using the Illumina/PacBio/BioNano/Nanopore or other next generation sequencing (NGS) platforms.

To facilitate detection of PCR products on a gel, the PCR primer may be labeled using Infra-Red dye (IRdye) or any conventional labeling method. In an alternative embodiment, other methods of amplification and screening may be used such as denaturing high pressure liquid chromatography (dHPLC), constant denaturant capillary electrophoresis (CDCE), temperature gradient capillary electrophoresis (TGCE) (see Li et al., Electrophoresis 23(10):1499-1511, 2002), or by fragmentation using enzymatic cleavage, such as used in the high throughput method described by Colbert et al. (2001), Triques et al. (2007), and in combination with next generation sequencing platforms as described above (Kumar et al., 2017).

In an alternate embodiment, Targeted Genotyping by sequencing (GBS) may be used to detect the mutation in the eIF4e and/or eIF(iso)4e gene The PCR amplification products may be incubated with an endonuclease that preferentially cleaves mismatches in heteroduplexes between wild type and mutant sequences which recognize and cleave at mismatches in a heteroduplex. Suitable endonucleases may include but are not limited to resolvases, RNases, bacteriophage T4 endonuclease VII, bacteriophage T7, endonuclease I, *Saccharomyces cerevisiae* endonuclease XI, *Saccharomyces cerevisiae* endonuclease X2, *Saccharomyces cerevisiae* endonuclease X3, SI nuclease, CEL I, PI nuclease, ENDO I nuclease or mung bean nuclease. In an embodiment, cleavage products are electrophoresed using an automated sequencing gel apparatus such as Licor (LICOR Inc.), and gel images are analyzed with the aid of a standard commercial image-processing program as per manufacturer's instructions.

The present inventors have determined that to achieve increased resistance in *papaya* as compared to wild type plants, mutations that alter and completely abolish eIF4e and/or eIF(iso)4e gene function are desirable. Preferred mutations include missense, nonsense and splice junction changes, including mutations that prematurely truncate the translation of the eIF4e and/or eIF(iso)4e protein from messenger RNA or make non-functional protein, such as those mutations that create a stop codon or codon change within the coding regions or splice junctions of the eIF4e and/or eIF(iso)4e gene. Such mutations include insertions, repeat sequences, modified open reading frames (ORFs), deletions, intron-exon splice junction point mutations and, most preferably, single nucleotide polymorphisms that lead to a loss of functional protein.

Thus, in one embodiment the present invention relates to a nucleic acid sequence (or gene) encoding a protein whose amino acid sequence is represented herein or encoding a protein derived from this (eIF4e and/or eIF(iso)4e) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and losing or partially losing the activity of the parent protein.

In an embodiment once an M2 plant having a mutated eIF4e and/or eIF(iso)4e sequence is identified, the mutations may be analyzed to determine its effect on the expression, translation, and/or activity of the protein. Thus, in an embodiment, the PCR fragment containing the mutation may be sequenced, using standard sequencing techniques, to determine the exact location of the mutation in relation to the overall eIF4e and/or eIF(iso)4e sequence. Each mutation is evaluated to predict its impact on protein function (i.e., completely tolerated to loss-of-function), molecular changes in bonding pattern of altered amino acid and altered nucleotide interaction in the new gene using in-silico bioinformatics tools such as SIFT, PARSESNP, CODDLE, CLUSTAL-W, BLASTP, BLASTN, PDB or other tools known in the art.

In an embodiment, if the initial assessment of a mutation in an M2 plant indicates it to be of a desirable nature and in a useful position within the eIF4e and/or eIF(iso)4e gene, then phenotypic analysis of the selected *papaya* plant containing that mutation maybe pursued using artificial inoculation with the PRSV strain and ELISA tests as well as growing the mutant plants in a disease hot spots where the incidence of PRSV infection is very high. Various methods may be used to obtain the line of papayas according to the present invention, first the selected M2 plant is backcrossed to the original parent at least twice or more using marker assisted selection (MAS) to create a backcross 1 (BC1) progeny plant to eliminate background mutations. The backcrossed BC1 plant may be self-pollinated to create a BC1F2 plant that maybe homozygous for the eIF4e and/or eIF(iso) 4e mutation. Several phenotypic characteristics of these homozygous eIF4e and eIF(iso)4e mutant plants may be assessed to determine if the mutation results in a useful and desirable genotypic and phenotypic changes in the *papaya* plant.

In an aspect, the present invention may provide novel mutations in the eIF4e and/or eIF(iso)4e gene of the *papaya* genome, such mutations may be created and identified according to various embodiments of the present invention. There is no previously reported mutation in the eIF4e gene (SEQ ID NO: 1,) and protein in *papaya* (SEQ ID NO: 6) beginning at nucleotide position 2112 (G2112A) (SEQ ID NO: 2) where a single nucleotide polymorphism (SNP) conversion of Guanine (G) to Adenine (A) in the eIF4e gene results in the formation of stop codon from Tryptophan (W) at the amino acid position of 140 leading to complete loss of protein and function (SEQ ID NO: 7). The STOP mutation (G2112A, W140*) in *papaya* eIF4e gene shows the stop of further translation beyond the protein sequence from amino acid position at 140. The mutation of the present invention results in a defective eIF4e gene leading to loss of complete transcription of the gene and translation into functional protein, thereby leading to the non-availability of the eIF4e translational initiation factor protein that is required for the multiplication of *papaya* ring spot viral RNA thereby leading to lack of PRSV symptoms and hence resistance. It has been shown that for successful PRSV infection, the cap protein of the PRSV physically interacts with the eIF4e and/or eIF(iso)4e protein for multiplication (Caranta et al., 1996, Piron et al., 2010).

In an embodiment, the present invention may also provide other mutations in eIF4e, which also leads to similar types of resistance towards PRSV in *papaya* as shown in Table 1.

Thus, an aspect of the present invention may provide a *papaya* plant, having a mutation in the eIF4e gene at the nucleotide position 2112 resulting in a stop codon on the 140-amino acid position of the SEQ ID NO: 7, resulting in a non-functional protein leading to increased resistance to the *papaya* ringspot virus, when compared to a wild type *papaya* plant.

As will be demonstrated in the examples, several physical characteristics of these homozygous eIF4e and/or eIF(iso)4e mutant plants may be assessed to determine if the mutation results in increased resistance to the *papaya* ringspot virus in the *papaya* plants. Mutant *papaya* plants are evaluated for degree of resistance as compared to normal (e. g., wild type) *papaya* plants. Such evaluation may include but not be limited to disease resistance screening bio-assays as well as phenotypic evaluations.

The PRSV screening technique was utilized to observe the resistance of the mutants towards the PRSV infection. The mutant seeds identified by TILLING and confirmed by sequencing were soaked in water and incubated in damped cloth for three days. Further the mutant seeds are sown in *papaya* media (coir and sand in 3:1 ratio). PRSV strains for inoculation were prepared by collecting the PRSV symptomatic *papaya* leaves, which are homogenized by crushing the collected leaves in mortar and pestle with inoculation buffer. The homogenized PRSV inoculum was subsequently inoculated on the leaves of wild type and mutant plants and observations were taken after 7, 14 and 21 days after inoculation (DAI). Various rating of infection was observed and severity was denoted by rating 0 for no infection and rating 4 for severe leaf mottling and stunting of plants. The level of resistance was determined based on the difference in rating of severity of virus infection between mutant plants and wild type plants. The value of the viral load was calculated using ELISA test and co-related to percentage (%) increase in mutation based on the severity rating. Thus a 0 rating may correlate to 100% increase in resistance as compared to wild type *papaya* plant.

Thus, in an embodiment, the increase in disease resistance in the *papaya* mutant of the present invention may range from 70%-100% in some cases, based on the type of mutation.

Thus, in an embodiment, the present invention may provide a *papaya* plant, having a mutation in the eIF4e and/or eIF(iso)4e gene such that the *papaya* has an increased resistance of up to 70%-100% as compared to a wild type *papaya* plant.

In an aspect of the present invention may provide eIF4e gene from *papaya* comprising a G2112A mutation; wherein the G2112A mutation comprises a nucleotide change within the eIF4e gene; and wherein the nucleotide change is identified according to SEQ ID NO: 2.

In an aspect of the present invention may provide novel mutations in the eIF(iso)4e gene, such mutations may be created and identified according to various embodiments of the present invention. There are no previously reported mutation in the eIF(iso)4e gene (SEQ ID NO: 20) and protein (SEQ ID NO: 24) in *papaya* beginning at nucleotide position 2046 (G2046A) (SEQ ID NO: 21) where a single nucleotide polymorphism (SNP) conversion of Guanine (G) to Adenine (A) in the eIF(iso)4e gene results in the formation of missense codon from Glycine (G) at the amino acid position of 105 to E leading to non-functional protein (G105E) (SEQ ID NO: 25). The non-tolerated missense mutation (G2046A) in *papaya* eIF(iso)4e gene shows the formation of non-functional protein due to change in protein sequence at the amino acid position 105 (G105E). The mutation of the present invention results in defective eIF (iso)4e gene leading to expression of the gene with a non-functional protein, leading to the non-availability of the eIF(iso)4e translational initiation factor protein for the multiplication of *papaya* ring spot viral RNA thereby leading to lack of PRSV symptoms and hence resistance. In an embodiment, the present invention may present other mutations in eIF(iso)4e which also leads to non-functional proteins leading to similar types of resistance towards PRSV in *papaya*.

In an alternate embodiment, the present invention may provide a *papaya* plant having increased disease resistance to the *papaya* ringspot virus as compared to a wild type *papaya* plant, comprising integrated in its genome (a) the nucleotide sequence set forth in SEQ ID NO: 2; (b) the nucleotide sequence set forth in SEQ ID NO:3, (c) a nucleotide sequence that encodes the polypeptide set forth in SEQ ID NO: 7; (d) a nucleotide sequence that encodes a polypeptide having at least 50%, 55%, 60%, 65%, 70%, 75%, 80%, 85%, 90%, or 95% sequence identity to the amino acid sequence set forth in SEQ ID NO: 7, wherein the polypeptide comprises at least one mutation described herein; (e) a nucleotide sequence having at least 50%, 55%, 60%, 65%, 70%, 75%, 80%, 85%, 90%, or 95% identity to the nucleotide sequence set forth in SEQ ID NO: 2 and encodes a polypeptide for translation initiation factor eIF4e as described herein; (f) a nucleotide sequence having at least 50%, 55%, 60%, 65%, 70%, 75%, 80%, 85%, 90%, or 95% identity to the nucleotide sequence set forth in SEQ ID NO: 3 and encodes a polypeptide for translation initiation factor eIF4e as described herein; or (g) a nucleotide sequence fully complementary to any one of (a) to (f).

In an alternate embodiment, the present invention may provide a *papaya* plant having increased disease resistance to the *papaya* ringspot virus infection as compared to a wild type *papaya*, comprising integrated in its genome (a) the nucleotide sequence set forth in SEQ ID NO: 21, (b) a nucleotide sequence that encodes the polypeptide set forth in SEQ ID NO: 25; (c) a nucleotide sequence that encodes a polypeptide having at least 50%, 55%, 60, 65%, 70%, 75%, 80%, 85%, 90%, or 95% sequence identity to amino acid sequence SEQ ID NO: 25, wherein the polypeptide comprises at least one mutation described herein; (d) a nucleotide sequence having at least 50%, 55%, 60, 65%, 70%, 75%, 80%, 85%, 90%, or 95% identity to the nucleotide sequence set forth in SEQ ID NO: 21 and encodes a polypeptide for translation initiation factor eIF(iso)4e as described herein; (e) a nucleotide sequence fully complementary to any one of (a) to (d).

In an aspect, the present invention may provide a *papaya* plant having increased resistance as compared to a wild type *papaya* plant to the *papaya* ringspot virus, comprising a mutation in the eIF4e gene, such that it introduced a stop codon in the corresponding nucleotide sequence such that it results in a non-functional polypeptide.

In an aspect, the present invention may provide a *papaya* plant having increased resistance as compared to a wild type *papaya* plant to the *papaya* ringspot virus, comprising a mutation in the eIF(iso)4e gene such that it results in a non-functional polypeptide.

Thus, an aspect of the present invention may provide methods of producing a *papaya* plant with increased resistance to *papaya* ringspot virus created by the steps comprising:
  a. treating *papaya* seeds with a mutagen and growing such plants;
  b. extracting DNA and/or RNA and analyzing progeny *papaya* plants to detect at least one mutation in at least one copy of a eIF4e and/or eIF(iso)4e gene/RNA transcript leading to non-functional eIF4e and/or eIF (iso)4e proteins;
  c. selecting progeny *papaya* plants carrying the mutation and that have increased resistance to *papaya* ringspot virus phenotypically;
  d. selecting directly for increased disease resistance by growing the progeny *papaya* plants in the presence of the disease.
  e. repeating the cycle of growing and culturing the progeny *papaya* plants to produce additional plants with increased resistance to *papaya* ringspot virus; and
  f. combining two lines both homozygous for the mutation in eIF4e gene present in the two parents to generate a hybrid; or combining the homozygous mutants in eIF (iso)4e gene present in the two parents to generate a hybrid; or combining the homozygous mutants in eIF4e and/or eIF(iso)4e genes present in two different parent plants to generate a hybrid by gene stacking.

Another aspect of the present invention may provide food and food products incorporating *papaya* fruits with increased resistance to the *papaya* ringspot virus caused by a mutation in the eIF4e and/or eIF(iso)4e gene leading to non-functional eIF4e and/or eIF(iso)4e proteins.

The present invention provides several advantages over the prior art. The process of TILLING results in the generation of stable mutant *papaya* plants that demonstrate an increased disease resistance to the *papaya* ringspot virus through novel mutations in the *papaya* genome. The method used in the present invention is both novel and inventive and cost efficient in comparison to other methods such as the transgenic methods and crossing with wild species with great difficulty described in the prior art. The *papaya* plants of the present invention results in the decrease in the use of agrochemicals for the control of the *papaya* ringspot virus vectors. The present invention results in a non-transgenic plant which is more acceptable by the consumers worldwide. These and other advantages will be further demonstrated in the examples below. The following examples are offered by way of illustration only, and not limitation thereof. It is to be understood that the mutations below are merely exemplary and that similar mutations leading to non-functional protein are also contemplated.

EXAMPLES

Example 1: Mutagenesis and DNA Extraction

*Papaya* seeds (10,000 seeds, called M0) of the breeding line (BVC#13243-2398) were washed with water and treated with 1M $KNO_3$ and then placed on a shaker (100 rpm) for overnight incubation. The mutagen ethyl methanesulfonate (EMS) was added under a fume hood to the imbibing seeds to final concentrations ranging from about 0.1% to about 1.6% (v/v). The treated seeds (called M1) were then incubated for a period of 6 to 12 hours, and the seeds were then rinsed with running water for approximately one hour. The mutagenized seeds were planted in potted trays and allowed to germinate in the nursery. Plants that were four to six weeks old were transferred to the field to grow to fully mature M1 plants. The flowers on the mature M1 plants were hermaphrodite and self-pollinated and then M2 seeds were collected from individual plants.

DNA extractions of M2 were performed using Qiagen plant DNA extraction kit following manufacturers instruction. Ten seeds per M2 families were sown in nursery pots inside a greenhouse and leaves were collected from four leaf stage M2 plants. The leaf samples were collected in 96-well collection plates with two 4 mm steel beads per well. The samples were frozen in liquid nitrogen and stored at −80° C. prior to DNA extraction. The protocol used for DNA extraction was from DNeasy 96-plant kit (Qiagen-Hilden, Germany). The samples were ground to powder with the help of the custom made vibrator shaker (Abraham et al., 2009). The extracted genomic DNA was run on 0.8% w/v agarose gel (Invitrogen) to check the quality. The quantity of M2 DNA was quantified with Nanodrop (Implen). The M2 DNA was normalized to 50 ng/l and 8-fold pooling plates were made for TILLING.

Example 2: Mutation Detection

Nested PCR was carried out by using target gene specific primers on 5 ng of *papaya* M2 genomic DNA. The first Ni PCR amplified product (1 µl) was used by diluting 1:10, which served as a template for the nested PCR, using 5'end infra-red dyes (IRD) labeled combinations of IRD700 and IRD800 M13 universal primers along with unlabeled N2 primers with M13 sequence and the section of Ni primer sequence Example 3: Bioinformatic Analysis CODDLE (Codons Optimized to Discover Deleterious Lesions,) was used to ascertain regions of the target gene in which G/C to A/T transitions, which are most likely to result in deleterious effects on the protein, had occurred. PARSESNP (Project Aligned Related Sequences and Evaluate SNPs,) was used to demonstrate the distribution of mutations within the target gene, and to indicate the nature of each single mutation. To predict the impact of the mutation on the target protein sequence, SIFT (Sorting Intolerant from Tolerant,) analysis and PPOPEN software analysis was done. ClustalW was utilized for Multiple Sequence Alignment of the gene of interest. Primers were designed according to the M13 TILLING system for each gene (Triques et al., 2007). TILLING primers for eIF4e (SEQ ID NOs: 8-19) and eIF(iso)4e (SEQ ID NOs: 26-49) were designed by Primer 3 software and further TILLING were carried out.

Example 4: Identification and Evaluation of Mutations (Tilling Screening)

M13 TILLING methodology from INRA-URGV (Triques et al., 2008; Triques et al., 2007), France was utilized to screen the *Papaya* mutant population. The workflow for M13 TILLING starts by designing sequence specific primers for the gene which it is intended for mutation screening. The PCR condition for the sequence specific reaction is an initial denaturation of 94° C. for 5 min, 35 cycles of denaturation at 94° C. for 10 sec, annealing at 55° C. for 15 sec, and extension at 72° C. for 1 min 30 sec, and a final extension of 72° C. for 5 min and cool down to 4° C. The Infrared labeled M13 universal primers were multiplexed by using the PCR product of the gene specific reaction as template. The PCR condition for the nested labeled reaction were as follows, initial denaturation of 94'C for 5 min and 10 cycles of denaturation at 94° C. for 15 sec, annealing at 60° C. for 30 sec, and extension at 72° C. for 1 min 30 sec (specific for the gene sequence), and 25 cycles of 94° C. for 15 sec, 50° C. for 30 sec and extension at 72° C. for 1 min 30 sec (specific for M13 universal primers) and a final extension of 72° C. for 5 min and cool down to 4° C. The labeled samples were then loaded into agarose gel for observing and obtaining an idea of how much PCR product should be taken for ENDO-I digestion. The samples were then passed through a RAMP reaction in which the samples were denatured at 94° C. and gradually cooled to 8° C. at the rate of −0.1° C. per second for enhanced formation of heteroduplex. The PCR product was then used for ENDO-I digestion at 45° C. for 20 minutes and 5 µl of 0.15 M EDTA (pH-8.0) was added to stop the reaction. The samples were then passed through the sephadex (GE, G-50, medium) for purification of the DNA samples. The sephadex were prepared by mixing equal quantities into the wells of Millipore filtration plate 94 well (Multiscreen-HV, MAHVN4550) with the help of sephadex column loader 45 l. After transferring the sephadex onto filtration plate, about 325 µl of sterile distilled water was added to make the sephadex to swell which requires an incubation of at least one hour. Excess water is centrifuged out by spinning at 500 G for 2 min. Sample plate is fit onto the filtration plate with 5 µl formamide loading dye. After stopping the ENDO-I digestion the samples are transferred into the Sephadex G-50 column and then centrifuged again to obtain the purified sample onto the formamide plates. The filtrate is further dried to 5 µl at 65° C. in a vacuum centrifuge concentrator for about an hour. Furthermore, the samples are denatured just before loading onto the Genetic Analyzer (Licor, 4300).

Acrylamide Gels on Licor 4300 System

TILLING gel plates were cleaned thoroughly and the gel plates and rails were paired respectively by taking the front and back plates placed on a flat surface. The plates were sandwiched with 0.25 mm spacers. 17.5 ml of $KB^+$ LICOR 6.5% gel matrix was taken and 196 µl of 10% Ammonium persulfate and 19.6 µl added and mixed gently. The mix was taken up in a 20 ml syringe and the gel was squeezed into the back plate by gentle tapping on the front plate. The plastic comb (0.25 mm) was inserted in between the plates and left to polymerize for about 90 min. After the polymerization the casting combs were removed and the glass plates were cleaned thoroughly with Milli-Q water to avoid the persistence of acrylamide gel on the outer surface. The cleaned plates were placed on to the Licor machine and the upper and lower tank was filled with 1×Tris Borate EDTA (TBE) (Licor) buffer. The notch was cleaned with a syringe and needle pre-run was started which goes on for 20 min at the following condition i.e. 1500V, 40W, 40 mA and 45° C. The denatured samples along with size-markers were denatured at 93° C. for 3 min and both were placed on ice. Using an 8-channel pipette 1.0 μl of the samples were loaded on to the cold sample-loading tray, which should be kept on ice while loading. The samples were absorbed by inserting the membrane comb in the tray for several seconds until complete absorption the comb was left to remain for 2 min at room temperature for drying. The notch was cleaned up with 1×TBE buffer and the comb inserted rapidly but gently at 45-degree angle with sample one on the left. The system was closed with the tank lids and wire. The run was started with the same conditions as the one done for pre-run for initially for four minutes and then the combs removed and the notch cleaned up with 1×TBE and the run restarted. TILLING images were detected by red and green spots for IRD700 and IRD800 respectively, which are represented by black and white picture for each fluorescent image using software provided with Licor 4300 TILLING was done on eIF4e and eIF(iso)4e gene on all the seven super pools (SP). And further deconvolution was done on probable mutants. The TILLING mutants were confirmed by sequencing and positions of mutations were confirmed. Genotyping by TILLING and sequencing was done to find whether the M2 seeds are Homozygous/Heterozygous/Wild type for the obtained mutations.

Table 1 below lists various mutations obtained after screening using TILLING method in eIF4e gene.

TABLE 1

| No. | Mutant Line No. | Code | Nature | Exon | Codon Change | Amino acid Change | SIFT Analysis | SIFT Score |
|---|---|---|---|---|---|---|---|---|
| | | | | | | Effect of Mutation | | |
| 1 | M2(0.3)-1709 | 2398 | (A)G2112A | Exon | UGG UGA | W140* | NA | NA |
| 2 | M2(0.3)-1220 | 2654 | (A)G2301A | Exon | GGA GAA | G173E | Not Tolerated | 0 |
| 3 | M2(0.4)-578 | 882 | (B)C2539T | Intronic | NA | NA | NA | NA |
| 4 | M2(0.4)-713 | 1114 | (B)A3393G | Intronic | NA | NA | NA | NA |
| 5 | M2(0.4)-638 | 974 | (B)A3553G | Intronic | NA | NA | NA | NA |

Table 2 below lists various mutations obtained after screening using TILLING method in eIF(iso)4e gene.

TABLE 2

| No. | Mutant Line No. | Code | Nature | Exon | Codon Change | Amino acid Change | SIFT Analysis | SIFT Score |
|---|---|---|---|---|---|---|---|---|
| | | | | | | Effect of Mutation | | |
| 1 | M2(0.4)-740 | 1170 | (B)C1912T | Intronic | NA | NA | NA | NA |
| 2 | M2(0.4)-882 | 1465 | (B)A1941G | Exon | UAC UGC | Y70C | Not Tolerated | 0 |
| 3 | M2(0.3)-1159 | 2503 | (A)A2117G | Intronic | NA | NA | NA | NA |
| 4 | M2(0.3)-1159 | 2503 | (A)A2147T | Intronic | NA | NA | NA | NA |
| 5 | M2(0.3)-1159 | 2503 | (A)C2118G | Intronic | NA | NA | NA | NA |
| 6 | M2(0.3)-1159 | 2503 | (A)C2391T | Intronic | NA | NA | NA | NA |
| 7 | M2(0.3)-1159 | 2503 | (A)G2239A | Exon | UUG UUA | L125= | NA | NA |
| 8 | M2(0.3)-1159 | 2503 | (A)A3576G | Intronic | NA | NA | NA | NA |
| 9 | M2(0.3)-1159 | 2503 | (A)C3408G | Intronic | NA | NA | NA | NA |
| 10 | M2(0.3)-49 | 117 | (A)A2040G | Exon | AAU AGU | N103S | Tolerated | 0.17 |
| 11 | M2(0.3)-181 | 387 | (A)A1998G | Exon | AAA AGA | K89R | Not Tolerated | 0 |
| 12 | M2(0.3)-704 | 1322 | (A)T1940C | Exon | UAC CAC | Y70H | Tolerated | 0.06 |
| 13 | M2(0.3)-87 | 189 | (A)T2098C | Exon | CUU CUC | L122= | NA | NA |
| 14 | M2(0.4)-1379 | 2460 | (B)G2095A | Exon | UGG UGA | W121* | NA | NA |
| 15 | M2(0.4)-1278 | 2286 | (B)C938T | Intronic | NA | NA | NA | NA |
| 16 | M2(0.3)-459 | 883 | (A)G1868A | Intronic | NA | NA | NA | NA |
| 17 | M2(0.3)-552 | 1038 | (A)G2046A | Exon | GGG GAG | G105E | Not Tolerated | 0 |

Example 5: Phenotypic Analysis of the Mutants by Artificial Inoculation

To prepare the test plants, pre-germination was done by soaking the seeds in water for 3 days and then transferred in a layer of damped cloth. Seeds were incubated for 3 days at room temperature. After pre-germination, the seeds were sown in individual polyethylene bags with papaya media (3:1-coir dust: sand). Seedlings were drenched with calcium nitrate once a week and with fungicide (promocarb hydrochloride/metalaxyl) were applied to prevent damping-off problems. Papaya mutant plants are grown to 8-leaf stage and the inoculum is prepared from PRSV infected symptomatic leaves. To be able to determine the suitable variety that will serve as good propagation host for PRSV, susceptible papaya controls were inoculated and their disease severity were assessed and compared. The suitable inoculum concentration was determined by comparing two inoculum dilutions (1:5 and 1:10). Virus titers of the first and second fully expanded leaf were compared using their ELISA values, leaf samples were collected at different days after inoculation (DAI), (7 DAI, 14 DAI and 21 DAI). Young, symptomatic leaves from PRSV infected seedlings were collected (preferably 14-21 days after inoculation) and homogenized in chilled inoculation buffer using a blender or a mortar and pestle in a 1:5 dilution (2 g of infected papaya leaves in 10 ml of inoculation buffer). Then virus homogenate was filtered through a layer of cheesecloth and 1:10 dilution was prepared from the 1:5 dilution. Thirty-days old seedlings were inoculated with ice-cold inoculum containing Celite (5 g/liter) on the upper leaf surface using sponge and washed with tap water after 5 minutes to remove the Celite and plant debris on the leaf surface (FIG. 1). The inoculation was repeated day after the first inoculation. Symptom development, disease severity and incidence were assessed at different times after inoculation (7, 14 and 21 DAI). Inoculated seedlings were rated based on disease severity 21 DAI using 0-4 scale below (Table 3):

TABLE 3

| Rating | Description |
| --- | --- |
| 0 | No symptom |
| 1 | Vein yellowing and/or mosaic |
| 2 | Mosaic + mottling |
| 3 | Mottling + leaf deformation |
| 4 | Severe mottling + shoe-stinging and/or stunting |

The value of the viral load was calculated and co-related to percentage (%) increase in mutation based on the severity rating. Thus a 0 rating may correlate to 99-100% increase in disease resistance as compared to wild type papaya plant. M2(0.3)-1709 is the eIF4e mutant papaya according to the present invention. M2(0.4)-740 is the eIF(iso)4e intronic mutation. M2(0.4)-882 is a eIF4e(iso) missense mutant with amino acid changes Y at position 70 to C (Y70C). The table below demonstrates observations (Table 4).

Table 4: Phenotypic observation of the mutant versus wild-type papaya plants for PRSV resistance.

TABLE 4

| Accession Code | Accession Name | BenchBio coordinates | Severity rating | OD value | ELISA Result |
| --- | --- | --- | --- | --- | --- |
| PH-02691 | EW 2398 (A) | M2(0.3)-1709 | 0 | 0.069 | Negative |
| | | M2(0.3)-1709 | 0 | 0.074 | Negative |
| | | M2(0.3)-1709 | 0 | 0.07 | Negative |
| | | M2(0.3)-1709 | 1 | 0.074 | Negative |
| | | M2(0.3)-1709 | 1 | 0.08 | Negative |
| | | M2(0.3)-1709 | 0 | 0.08 | Negative |
| PH-02692 | EW 2654 (A) | WILD TYPE | 4 | 0.332 | Positive |
| PH-02693 | EW 1170 (B) | M2(0.4)-740 | 4 | 0.922 | Positive |
| PH-02694 | EW 1465 (B) | M2(0.4)-882 | 4 | 0.935 | Positive |
| PH-02695 | EW 2503 (A) | WILD TYPE | 4 | 0.787 | Positive |
| PH-1301 | S-check | WILD TYPE | 4 | 1.023 | Positive |
| | | | Healthy check 1 | 0.079 | |
| | | | Healthy check 2 | 0.08 | |
| | | | Healthy check 3 | 0.08 | |
| | | | Buffer | 0.068 | |
| | | | Positive value | ≥0.199* | |
| | | | Positive check | 0.554 | |

*Average of healthy checks X 2.5

Figure 2:
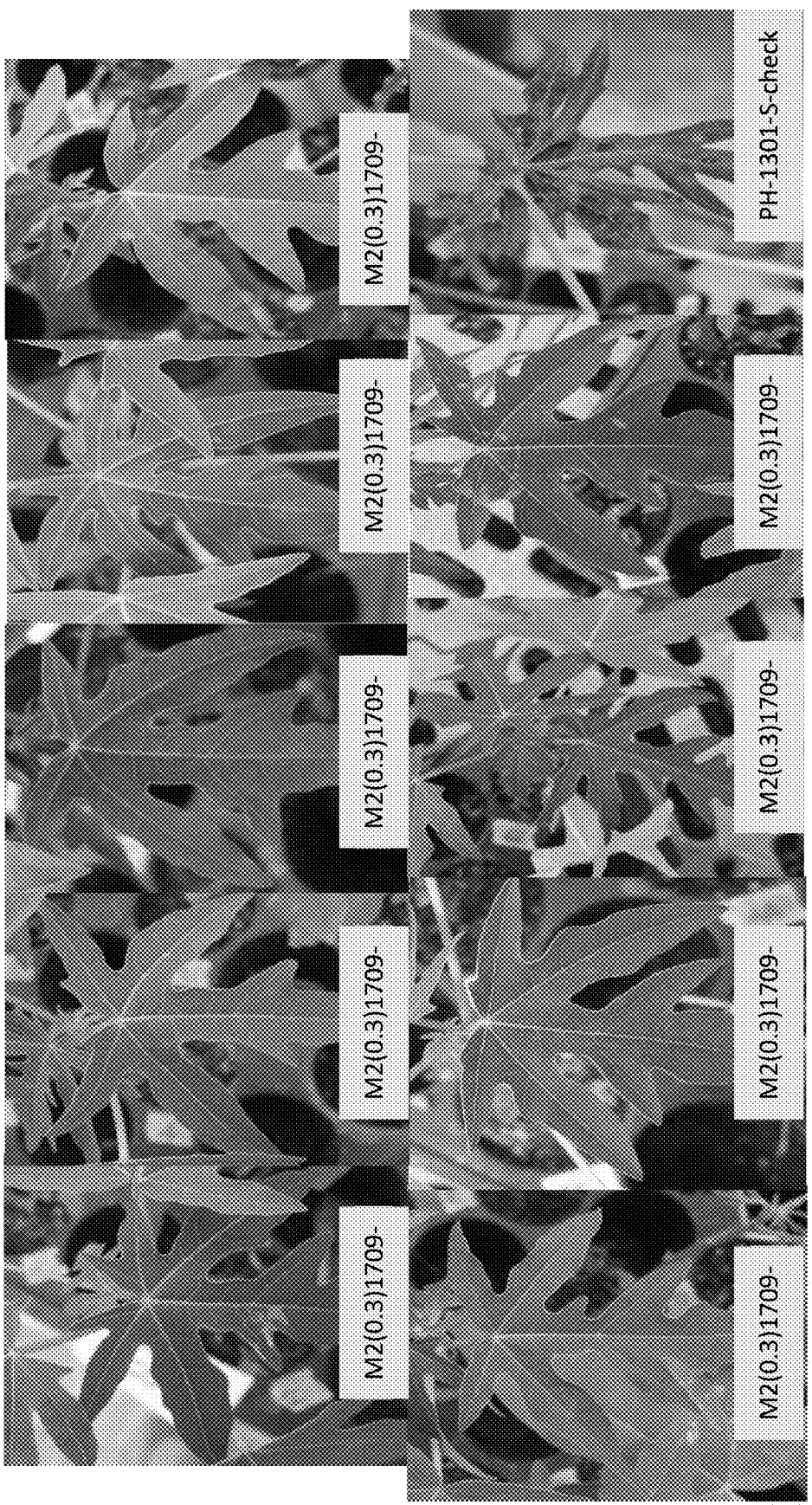
FIG. 2 shows *Papaya* M2(0.3)-1709 mutant seedlings demonstrating resistance to *papaya* ringspot virus along with infection ratings; S-check is the susceptible check i.e. a positive control.

The above table clearly demonstrates, eIF4e mutants with increased resistance compared to wild type and other mutants (M2(0.4)-740, 882) which served as positive control plants. It is clearly observed that all resistant plants have low OD values of viral load at 0.069, translating to 100% increased resistance over wild type susceptible plant which showed high OD values of viral load at 0.787. When compared with positive controls, some mutant plants showed a 90% increase in resistance. All the homozygous mutants confirmed by TILLING and by genotyping showed no symptoms after the inoculation, whereas the positive control (susceptible check) showed severe mottling and stunting effect in the papaya plants typical of PRSV infection (FIG. 2). In doing standard ELISA, negative controls have to be included, these negative controls refer to the healthy checks. Three healthy checks were taken from seedlings which are not challenged by PRSV. To calculate the threshold value in which we can declare that the sample is infected by PRSV, we take the average readings of the 3 healthy checks and multiply it by 2.5. And this calculated value (=positive value) is the threshold. Anything that is higher or equal to the "positive value" means it is infected with PRSV. If the value is lower than the threshold, then it is declared not infected by PRSV. The positive check is the positive control—leaves coming from PRSV-infected plants.

We claim:

1. A *papaya* plant having increased resistance to *Papaya* Ringspot virus as compared to a wild type papaya plant, wherein the plant having increased resistance comprises a mutated eIF4e gene, and wherein the mutated eIF4e gene comprises a G to A substitution at position 2112 (G2112A) and leads to a non-functional eIF4e protein, wherein the mutated eIF4e gene comprises the nucleotide sequence as set forth in SEQ ID NO: 2.

2. The *papaya* plant according to claim 1, wherein the plant comprises whole plant, plant cells, seeds, and/or fruits.

3. The *papaya* plant according to claim 1, wherein the mutation is a non-transgenic mutation.

4. The papaya plant according to claim 1, wherein the mutation is an induced mutation.

5. The papaya plant according to claim 1, wherein the mutation introduces a stop codon in the nucleotide sequence of eIF4e gene.

\* \* \* \* \*

SEQUENCE LISTING

<160> NUMBER OF SEQ ID NOS: 49

<210> SEQ ID NO 1
<211> LENGTH: 4609
<212> TYPE: DNA
<213> ORGANISM: Carica papaya
<220> FEATURE:
<221> NAME/KEY: misc_feature
<222> LOCATION: (601)..(1820)
<223> OTHER INFORMATION: n is a, c, g, or t

<400> SEQUENCE: 1

| | | | | | | |
|---|---|---|---|---|---|---|
| gacataacag | caattttacc | cagaaggtcc | cctttcatgt | ccattttag | gaaaaagggg | 60 |
| gaaggaaatt | cttgaagaaa | cctcttcaga | gcaggtgaaa | atacagagaa | gagagtagga | 120 |
| atcgggaaga | cgccatggta | gtagaaggaa | cccccaaact | attatccaca | tccgtcgcgg | 180 |
| aagacaaacc | caatcccaat | accgcgaacc | ctaattctag | acctcgtggc | gacgaggaag | 240 |
| acgagggggcc | ggaggaaggg | gagattgtgg | atgaggatga | atccaagaga | tcatcagccg | 300 |
| ttttgctcca | gccgcatcct | ctcgagcatc | catggacatt | ctggtttgat | aacttctctg | 360 |
| ccaaatccaa | gcaagccaca | tggggtagct | ctatgcgatc | cgtgtatacg | ttccgaactg | 420 |
| ttgaggagtt | ctggagattt | ggtgtcgagg | ttttttttata | gtatgatctt | gtttaggtta | 480 |
| gatattgggc | actcatattg | tttattggta | gataggtaga | ggagatttca | tgcttgtttg | 540 |
| atagaaaatt | gtgagagatg | aaaggctaag | agtgctaagc | ggaaagaaac | tatgtttttt | 600 |
| nnnnnnnnnn | nnnnnnnnnn | nnnnnnnnnn | nnnnnnnnnn | nnnnnnnnnn | nnnnnnnnnn | 660 |
| nnnnnnnnnn | nnnnnnnnnn | nnnnnnnnnn | nnnnnnnnnn | nnnnnnnnnn | nnnnnnnnnn | 720 |
| nnnnnnnnnn | nnnnnnnnnn | nnnnnnnnnn | nnnnnnnnnn | nnnnnnnnnn | nnnnnnnnnn | 780 |
| nnnnnnnnnn | nnnnnnnnnn | nnnnnnnnnn | nnnnnnnnnn | nnnnnnnnnn | nnnnnnnnnn | 840 |
| nnnnnnnnnn | nnnnnnnnnn | nnnnnnnnnn | nnnnnnnnnn | nnnnnnnnnn | nnnnnnnnnn | 900 |
| nnnnnnnnnn | nnnnnnnnnn | nnnnnnnnnn | nnnnnnnnnn | nnnnnnnnnn | nnnnnnnnnn | 960 |
| nnnnnnnnnn | nnnnnnnnnn | nnnnnnnnnn | nnnnnnnnnn | nnnnnnnnnn | nnnnnnnnnn | 1020 |
| nnnnnnnnnn | nnnnnnnnnn | nnnnnnnnnn | nnnnnnnnnn | nnnnnnnnnn | nnnnnnnnnn | 1080 |
| nnnnnnnnnn | nnnnnnnnnn | nnnnnnnnnn | nnnnnnnnnn | nnnnnnnnnn | nnnnnnnnnn | 1140 |
| nnnnnnnnnn | nnnnnnnnnn | nnnnnnnnnn | nnnnnnnnnn | nnnnnnnnnn | nnnnnnnnnn | 1200 |
| nnnnnnnnnn | nnnnnnnnnn | nnnnnnnnnn | nnnnnnnnnn | nnnnnnnnnn | nnnnnnnnnn | 1260 |
| nnnnnnnnnn | nnnnnnnnnn | nnnnnnnnnn | nnnnnnnnnn | nnnnnnnnnn | nnnnnnnnnn | 1320 |
| nnnnnnnnnn | nnnnnnnnnn | nnnnnnnnnn | nnnnnnnnnn | nnnnnnnnnn | nnnnnnnnnn | 1380 |
| nnnnnnnnnn | nnnnnnnnnn | nnnnnnnnnn | nnnnnnnnnn | nnnnnnnnnn | nnnnnnnnnn | 1440 |
| nnnnnnnnnn | nnnnnnnnnn | nnnnnnnnnn | nnnnnnnnnn | nnnnnnnnnn | nnnnnnnnnn | 1500 |
| nnnnnnnnnn | nnnnnnnnnn | nnnnnnnnnn | nnnnnnnnnn | nnnnnnnnnn | nnnnnnnnnn | 1560 |
| nnnnnnnnnn | nnnnnnnnnn | nnnnnnnnnn | nnnnnnnnnn | nnnnnnnnnn | nnnnnnnnnn | 1620 |
| nnnnnnnnnn | nnnnnnnnnn | nnnnnnnnnn | nnnnnnnnnn | nnnnnnnnnn | nnnnnnnnnn | 1680 |
| nnnnnnnnnn | nnnnnnnnnn | nnnnnnnnnn | nnnnnnnnnn | nnnnnnnnnn | nnnnnnnnnn | 1740 |
| nnnnnnnnnn | nnnnnnnnnn | nnnnnnnnnn | nnnnnnnnnn | nnnnnnnnnn | nnnnnnnnnn | 1800 |
| nnnnnnnnnn | nnnnnnnnnn | gtgagcacaa | gattttgttt | tgtcaaggtt | tatacttcaa | 1860 |
| aagctagatc | caacatccgg | tgctgttgtc | tattgctttt | ctgatgtttc | tctaccacag | 1920 |
| actgtcaaat | ctgcgtttgt | caacattttc | ctcaatgttt | aacagtcttg | ctttaaattt | 1980 |

-continued

```
tatttccatt cagcccttta caataatata catcatccaa gcaagttggc tgttggagca    2040 gactttatt  gcttcaaaca taaaattgaa ccaaaatggg aggaccctgt tgtgctaat     2100 ggaggaaaat ggactatgaa tttccaaaga ggaaaatctg atacctgttg gttgtatacg    2160
gtatgcctca ctatctttgg tatctagctc cgtgtagcat tcactttgta tatcatttat    2220
ggactctgat tgccgtgcat gctggttcta gttgctggca atgattggag aacagtttga    2280
tcatggagat gaaatttgcg gagttgtcgt aatgtcaga  ggcaggcaag agaagatagc    2340
cttatggacc aaaaatgctg caaacgaggc tgctcaggta aaattgaatg acaaagctaa    2400
ctgatgttta tatctctgtt ataatggtct tatattttgg gtggtcttag ttattttaac    2460
gatttgctta atttaattat ttagttctcc tggacttgct ttatgttttc cttagttaat    2520
tgtgatcact ttcctattct aatagtagca ttatttgttc ctcattgtat tggtatagat    2580
accagtactt cgggaaattc ctattctaac tcttttggga aaaagtttct tcagactcta    2640
tgaatactct tgtcatctca tctttgaaat catttgagtc gatataggtt actctgggaa    2700
ttttcttaat atcttggttt ggtgattcaa tagtgtaatg gtcaagaagc taggtgtgg    2760 tagctaaggc agcccagatc cctaagtgga ctaaataacc caaattcatc ttacatcaac    2820
ttgtatactt tgagagaatt tcttgctctt ggcttcatta ggcttgacta ttttatgcta    2880
atagacagat tcgttgtatt ccccatgatg atttgcttct gtttaattta ttttatcaaa    2940
gtgttaccgg tggaaaacta aaagataag  aagtaattat ggactgtaaa atattgattc    3000
ctataacatt agtggaccat gtgatgaacc atgtatatac gccattgcac agaatcattg    3060
aaatagaatg gcatgtaagt ttgttgaaag tgtaagttac tattttgatg aatgattaga    3120
tggcttgcct gcaacttgct atgacaaaat gagatatttg gaatgggatg cacgtcatct    3180
tcaagatgag taggcttctt ggtgttgcct acccaaccat ggtgataaga caattaattt    3240
aaaatacaaa ctcgtgaggc atgaataatt gcatacatta gtcgaggagt ttgcatgttt    3300
tcttaaataa atttcttgtt gcagatgagc attgggaagc agtggaagga atttcttgat    3360
tacaatgaca ccatggggtt catatttcac gtaagaattt tgtgttcaaa tttaggcaca    3420
caaatttata tttgtccctg gcttattggt ggcagctcga gtaacttctt ggttttctt    3480 ttcaggagga tgcaaagaag cttgagagag ctgctaagaa tcgctactcg gtatgaaatt    3540
tgctggttgt tcagcattcg ccacaggaat tctaaatgtt ggattcatat ccgaacctta    3600
gaatgacttg tacttacctt ctttccgtaa taggatagtt ttctcaggct attaggatag    3660
ttggataaaa gcaatgctgc acctttctc  ttcatatcct agtttgggaa ttcatgccac    3720
caaaaattgc cgctttattc tggtttaatc aaagattaat gttgtcaata gtttctcggt    3780
cgaaagagtt ttctcttcat atatcctatt tgaatggtta ctaaaatgta ataacctggg    3840
tgcaaatctg gatactggga tgtatgtttt ctttctgcag gtcacagagt acataattgc    3900 aaattttct  gatttatgca ttaaaaatgc tgctttcagt ttctctggga acttttgttt    3960
aatggaagca gtgatggttt gaattaagta cactctgata ctctttcttt tttgaagccc    4020
atgttgttta actaaagatt ttcaagaaaa ggaaaagatt tctcatggag aagaaatatt    4080
ctttgggtga agagtgagag ggtggttgag attatttgtc taatgaattt actgaacaac    4140
ttatttcaca ctcacttata gttgataata tatgataaac tatacaatac tgtaataatt    4200
atatatctgt attaatattt gtgtatgcat gtgtgtctat agctgcaata cagtaatatg    4260
tataatattg tcttgtgata tgtatgatta atctctaata tttgtaatgt aatatgtata    4320
```

| | |
|---|---:|
| attaatcact aagtttgaaa ctacacgttg aatcaacaat atatgtaaac ataaattttt | 4380 |
| caaaaaaaat ttcgaagaaa aaatgttgtg tatgattttta cttggatgat tttttaatat | 4440 |
| gttaagagag agatatttcg agaagaaata gtctctcatt taatatctat aataattaga | 4500 |
| ttatggatct aggtcaaaaa acccgatttg aatatttttt tgatccgaat attaagattt | 4560 |
| ataagttaat ggatataaaa agtttagaat gctattaaag aatttataa | 4609 |

<210> SEQ ID NO 2
<211> LENGTH: 4609
<212> TYPE: DNA
<213> ORGANISM: Carica papaya
<220> FEATURE:
<221> NAME/KEY: misc_feature
<222> LOCATION: (601)..(1820)
<223> OTHER INFORMATION: n is a, c, g, or t

<400> SEQUENCE: 2

| | |
|---|---:|
| gacataacag caattttacc cagaaggtcc cctttcatgt ccattttttag gaaaaagggg | 60 |
| gaaggaaatt cttgaagaaa cctcttcaga gcaggtgaaa atacagagaa gagagtagga | 120 |
| atcgggaaga cgccatggta gtagaaggaa ccccccaaact attatccaca tccgtcgcgg | 180 |
| aagacaaacc caatcccaat accgcgaacc ctaattctag acctcgtggc gacgaggaag | 240 |
| acgaggggcc ggaggaaggg gagattgtgg atgaggatga atccaagaga tcatcagccg | 300 |
| ttttgctcca gccgcatcct ctcgagcatc catggacatt ctggtttgat aacttctctg | 360 |
| ccaaatccaa gcaagccaca tggggtagct ctatgcgatc cgtgtatacg ttccgaactg | 420 |
| ttgaggagtt ctgagagattt ggtgtcgagg tttttttata gtatgatctt gtttaggtta | 480 |
| gatattgggc actcatattg tttattggta gataggtaga ggagatttca tgcttgtttg | 540 |
| atagaaaatt gtgagagatg aaaggctaag agtgctaagc ggaaagaaac tatgtttttt | 600 |
| nnnnnnnnnn nnnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |

```
nnnnnnnnnn nnnnnnnnnn nnnnnnnnnn nnnnnnnnnn nnnnnnnnnn nnnnnnnnnn    1800
nnnnnnnnnn nnnnnnnnnn gtgagcacaa gattttgttt tgtcaaggtt tatacttcaa    1860
aagctagatc caacatccgg tgctgttgtc tattgctttt ctgatgtttc tctaccacag    1920
actgtcaaat ctgcgtttgt caacattttc ctcaatgttt aacagtcttg ctttaaattt    1980
tatttccatt cagcccttta caataatata catcatccaa gcaagttggc tgttggagca    2040
gacttttatt gcttcaaaca taaaattgaa ccaaaatggg aggaccctgt ttgtgctaat    2100
ggaggaaaat ggactatgaa tttccaaaga ggaaaatctg atacctgttg gttgtatacg    2160
gtatgcctca ctatctttgg tatctagctc cgtgtagcat tcactttgta tatcatttat    2220
ggactctgat tgccgtgcat gctggttcta gttgctggca atgattggag aacagtttga    2280
tcatggagat gaaatttgcg gagttgtcgt gaatgtcaga ggcaggcaag agaagatagc    2340
cttatggacc aaaaatgctg caaacgaggc tgctcaggta aaattgaatg acaaagctaa    2400
ctgatgttta tatctctgtt ataatggtct tatattttgg gtggtcttag ttattttaac    2460
gatttgctta atttaattat ttagttctcc tggacttgct ttatgttttc cttagttaat    2520
tgtgatcact ttcctattct aatagtagca ttatttgttc ctcattgtat tggtatagat    2580
accagtactt cgggaaattc ctattctaac tcttttgga aaagtttct tcagactcta    2640 tgaatactct tgtcatctca tctttgaaat catttgagtc gatataggtt actctgggaa    2700
ttttcttaat atcttggttt ggtgattcaa tagtgtaatg gtcaagaagc ctaggtgtgg    2760
tagctaaggc agcccagatc cctaagtgga ctaaataacc caattcatc ttacatcaac    2820 ttgtatactt tgagagaatt tcttgctctt ggcttcatta ggcttgacta ttttatgcta    2880
atagacagat tcgttgtatt ccccatgatg atttgcttct gtttaattta ttttatcaaa    2940
gtgttaccgg tggaaaacta aaaagataag aagtaattat ggactgtaaa atattgattc    3000
ctataacatt agtggaccat gtgatgaacc atgtatatac gccattgcac agaatcattg    3060
aaatagaatg gcatgtaagt ttgttgaaag tgtaagttac tattttgatg aatgattaga    3120
tggcttgcct gcaacttgct atgacaaaat gagatatttg gaatgggatg cacgtcatct    3180
tcaagatgag taggcttctt ggtgttgcct acccaaccat ggtgataaga caattaattt    3240
aaaatacaaa ctcgtgaggc atgaataatt gcatacatta gtcgaggagt ttgcatgttt    3300
tcttaaataa atttcttgtt gcagatgagc attgggaagc agtggaagga atttcttgat    3360
tacaatgaca ccatggggtt catatttcac gtaagaattt tgtgttcaaa tttaggcaca    3420
caaatttata tttgtccctg gcttattggt ggcagctcga gtaacttctt ggttttctt    3480 ttcaggagga tgcaaagaag cttgagagag ctgctaagaa tcgctactcg gtatgaaatt    3540
tgctggttgt tcagcattcg ccacaggaat tctaaatgtt ggattcatat ccgaacctta    3600
gaatgacttg tacttacctt cttccgtaa taggatagtt ttctcaggct attaggatag    3660
ttggataaaa gcaatgctgc accttttctc ttcatatcct agtttgggaa ttcatgccac    3720
caaaaattgc cgctttattc tggtttaatc aaagattaat gttgtcaata gtttctcggt    3780
cgaaagagtt ttctcttcat atatcctatt tgaatggtta ctaaaatgta ataacctggg    3840
tgcaaatctg gatactggga tgtatgtttt ctttctgcag gtcacagagt acataattgc    3900
aaatttttct gatttatgca ttaaaaatgc tgctttcagt ttctctggga acttttgttt    3960
aatggaagca gtgatggttt gaattaagta cactctgata ctctttcttt tttgaagccc    4020
atgttgttta actaaagatt ttcaagaaaa ggaaaagatt tctcatggag aagaaatatt    4080
```

```
ctttgggtga agagtgagag ggtggttgag attatttgtc taatgaattt actgaacaac    4140
ttatttcaca ctcacttata gttgataata tatgataaac tatacaatac tgtaataatt    4200
atatatctgt attaatattt gtgtatgcat gtgtgtctat agctgcaata cagtaatatg    4260
tataatattg tcttgtgata tgtatgatta atctctaata tttgtaatgt aatatgtata    4320
attaatcact aagtttgaaa ctacacgttg aatcaacaat atatgtaaac ataaattttt    4380
caaaaaaat ttcgaagaaa aaatgttgtg tatgatttta cttggatgat tttttaatat     4440
gttaagagag agatatttcg agaagaaata gtctctcatt taatatctat aataattaga    4500
ttatggatct aggtcaaaaa acccgatttg aatattttt tgatccgaat attaagattt     4560
ataagttaat ggatataaaa agtttagaat gctattaaag aatttataa                4609
```

<210> SEQ ID NO 3
<211> LENGTH: 4609
<212> TYPE: DNA
<213> ORGANISM: Carica papaya
<220> FEATURE:
<221> NAME/KEY: misc_feature
<222> LOCATION: (601)..(1820)
<223> OTHER INFORMATION: n is a, c, g, or t

<400> SEQUENCE: 3

```
gacataacag caattttacc cagaaggtcc cctttcatgt ccattttag gaaaaagggg      60
gaaggaaatt cttgaagaaa cctcttcaga gcaggtgaaa atacagagaa gagagtagga    120
atcgggaaga cgccatggta gtagaaggaa ccccccaaact attatccaca tccgtcgcgg   180
aagacaaacc caatcccaat accgcgaacc ctaattctag acctcgtggc gacgaggaag    240
acgaggggcc ggaggaaggg gagattgtgg atgaggatga atccaagaga tcatcagccg    300
ttttgctcca gccgcatcct ctcgagcatc catggacatt ctggtttgat aacttctctg    360
ccaaatccaa gcaagccaca tggggtagct ctatgcgatc cgtgtatacg ttccgaactg    420
ttgaggagtt ctggagattt ggtgtcgagg ttttttata gtatgatctt gtttaggtta     480
gatattgggc actcatattg tttattggta gataggtaga ggagatttca tgcttgtttg    540
atagaaaatt gtgagagatg aaaggctaag agtgctaagc ggaaagaaac tatgtttttt    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
```

```
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn gtgagcacaa gattttgttt tgtcaaggtt tatacttcaa    1860
aagctagatc caacatccgg tgctgttgtc tattgctttt ctgatgtttc tctaccacag    1920
actgtcaaat ctgcgtttgt caacattttc ctcaatgttt aacagtcttg ctttaaattt    1980
tatttccatt cagcccttta caataatata catcatccaa gcaagttggc tgttggagca    2040
gacttttatt gcttcaaaca taaaattgaa ccaaaatggg aggaccctgt tgtgctaat     2100 ggaggaaaat ggactatgaa tttccaaaga ggaaaatctg atacctgttg gttgtatacg    2160
gtatgcctca ctatctttgg tatctagctc cgtgtagcat tcactttgta tatcatttat    2220
ggactctgat tgccgtgcat gctggttcta gttgctggca atgattggag aacagtttga    2280
tcatggagat gaaatttgcg gagttgtcgt aatgtcaga ggcaggcaag agaagatagc     2340
cttatggacc aaaaatgctg caaacgaggc tgctcaggta aaattgaatg acaaagctaa    2400
ctgatgttta tatctctgtt ataatggtct tatattttgg gtggtcttag ttattttaac    2460
gatttgctta atttaattat ttagttctcc tggacttgct ttatgttttc cttagttaat    2520
tgtgatcact ttcctattct aatagtagca ttatttgttc ctcattgtat tggtatagat    2580
accagtactt cgggaaattc ctattctaac tcttttgga aaaagtttct tcagactcta     2640
tgaatactct tgtcatctca tctttgaaat catttgagtc gatataggtt actctgggaa    2700
ttttcttaat atcttggttt ggtgattcaa tagtgtaatg gtcaagaagc ctaggtgtgg    2760
tagctaaggc agcccagatc cctaagtgga ctaaataacc caattcatc ttacatcaac     2820 ttgtatactt tgagagaatt tcttgctctt ggcttcatta ggcttgacta ttttatgcta    2880
atagacagat tcgttgtatt ccccatgatg atttgcttct gtttaattta ttttatcaaa    2940
gtgttaccgg tggaaaacta aaaagataag aagtaattat ggactgtaaa atattgattc    3000
ctataacatt agtggaccat gtgatgaacc atgtatatac gccattgcac agaatcattg    3060
aaatagaatg gcatgtaagt tgttgaaag tgtaagttac tattttgatg aatgattaga     3120
tggcttgcct gcaacttgct atgacaaaat gagatatttg gaatgggatg cacgtcatct    3180
tcaagatgag taggcttctt ggtgttgcct acccaaccat ggtgataaga caattaattt    3240
aaaatacaaa ctcgtgaggc atgaataatt gcatacatta gtcgaggagt ttgcatgttt    3300
tcttaaataa atttcttgtt gcagatgagc attgggaagc agtggaagga atttcttgat    3360
tacaatgaca ccatggggtt catatttcac gtaagaattt tgtgttcaaa tttaggcaca    3420
caaatttata tttgtccctg gcttattggt ggcagctcga gtaacttctt ggttttctt    3480 ttcaggagga tgcaaagaag cttgagagag ctgctaagaa tcgctactcg gtatgaaatt    3540
tgctggttgt tcagcattcg ccacaggaat tctaaatgtt ggattcatat ccgaacctta    3600
gaatgacttg tacttacctt cttccgtaa taggatagtt ttctcaggct attaggatag     3660
ttggataaaa gcaatgctgc accttttctc ttcatatcct agtttgggaa ttcatgccac    3720
caaaaattgc cgcttattc tggtttaatc aaagattaat gttgtcaata gtttctcggt     3780
cgaaagagtt ttctcttcat atatcctatt tgaatggtta ctaaaatgta ataacctggg    3840
```

```
tgcaaatctg gatactggga tgtatgtttt ctttctgcag gtcacagagt acataattgc    3900
aaatttttct gatttatgca ttaaaaatgc tgctttcagt ttctctggga acttttgttt    3960
aatggaagca gtgatggttt gaattaagta cactctgata ctctttcttt tttgaagccc    4020
atgttgttta actaaagatt ttcaagaaaa ggaaaagatt tctcatggag aagaaatatt    4080
ctttgggtga agagtgagag ggtggttgag attatttgtc taatgaattt actgaacaac    4140
ttatttcaca ctcacttata gttgataata tatgataaac tatacaatac tgtaataatt    4200
atatatctgt attaatattt gtgtatgcat gtgtgtctat agctgcaata cagtaatatg    4260
tataatattg tcttgtgata tgtatgatta atctctaata tttgtaatgt aatatgtata    4320
attaatcact aagtttgaaa ctacacgttg aatcaacaat atatgtaaac ataaattttt    4380
caaaaaaaat ttcgaagaaa aaatgttgtg tatgatttta cttggatgat ttttttaatat   4440 gttaagagag agatatttcg agaagaaata gtctctcatt taatatctat aataattaga    4500
ttatggatct aggtcaaaaa acccgatttg aatattttt tgatccgaat attaagattt     4560
ataagttaat ggatataaaa agtttagaat gctattaaag aatttataa                4609
```

<210> SEQ ID NO 4
<211> LENGTH: 1155
<212> TYPE: DNA
<213> ORGANISM: Carica papaya

<400> SEQUENCE: 4

```
gacataacag caattttacc cagaaggtcc cctttcatgt ccattttag gaaaaagggg       60 gaaggaaatt cttgaagaaa cctcttcaga gcaggtgaaa atacagagaa gagagtagga    120
atcgggaaga cgccatggta gtagaaggaa cccccaaact attatccaca tccgtcgcgg    180
aagacaaacc caatcccaat accgcgaacc ctaattctag acctcgtggc gacgaggaag    240
acgaggggcc ggaggaaggg gagattgtgg atgaggatga atccaagaga tcatcagccg    300
ttttgctcca gccgcatcct ctcgagcatc catggacatt ctggtttgat aacttctctg    360
ccaaatccaa gcaagccaca tggggtagct ctatgcgatc cgtgtatacg ttccgaactg    420
ttgaggagtt ctggagcctt tacaataata tacatcatcc aagcaagttg gctgttggag    480
cagactttta ttgcttcaaa cataaaattg aaccaaaatg ggaggaccct gtttgtgcta    540
atggaggaaa atggactatg aatttccaaa gaggaaaatc tgatacctgt tggttgtata    600
cgttgctggc aatgattgga gaacagtttg atcatggaga tgaaatttgc ggagttgtcg    660
tgaatgtcag aggcaggcaa gagaagatag cctatggac caaaaatgct gcaaacgagg    720
ctgctcagat gagcattggg aagcagtgga aggaatttct tgattacaat gacaccatgg    780
ggttcatatt tcacgaggat gcaagaagc ttgagagagc tgctaagaat cgctactcgg     840
tatgaaattt gctggttgtt cagcattcgc cacaggaatt ctaaatgttg gattcatatc    900
cgaaccttag aatgacttgt acttaccttc tttccgtaat aggatagttt ctcaggcta     960 ttaggatagt tggataaaag caatgctgca ccttttctct tcatatccta gtttgggaat   1020
tcatgccacc aaaaattgcc gctttattct ggtttaatca agattaatg ttgtcaatag    1080 tttctcggtc gaaagagttt tctcttcata tatcctatttt gaatggttac taaaatgtaa   1140
caaaaaaaaa aaaaa                                                     1155
```

<210> SEQ ID NO 5
<211> LENGTH: 1155
<212> TYPE: DNA
<213> ORGANISM: Carica papaya

<400> SEQUENCE: 5

```
gacataacag caattttacc cagaaggtcc cctttcatgt ccatttttag gaaaaagggg      60
gaaggaaatt cttgaagaaa cctcttcaga gcaggtgaaa atacagagaa gagagtagga    120
atcgggaaga cgccatggta gtagaaggaa cccccaaact attatccaca tccgtcgcgg    180
aagacaaacc caatcccaat accgcgaacc ctaattctag acctcgtggc gacgaggaag    240
acgaggggcc ggaggaaggg gagattgtgg atgaggatga atccaagaga tcatcagccg    300
ttttgctcca gccgcatcct ctcgagcatc catggacatt ctggtttgat aacttctctg    360
ccaaatccaa gcaagccaca tggggtagct ctatgcgatc cgtgtatacg ttccgaactg    420
ttgaggagtt ctggagcctt acaataata tacatcatcc aagcaagttg gctgttggag     480
cagactttta ttgcttcaaa cataaaattg aaccaaaatg gaggaccct gtttgtgcta     540
atggaggaaa atgaactatg aatttccaaa gaggaaaatc tgatacctgt tggttgtata    600
cgttgctggc aatgattgga gaacagtttg atcatggaga tgaaatttgc ggagttgtcg    660
tgaatgtcag aggcaggcaa gagaagatag ccttatggac caaaaatgct gcaaacgagg    720
ctgctcagat gagcattggg aagcagtgga aggaatttct tgattacaat gacaccatgg    780
ggttcatatt tcacgaggat gcaaagaagc ttgagagagc tgctaagaat cgctactcgg    840
tatgaaattt gctggttgtt cagcattcgc cacaggaatt ctaaatgttg gattcatatc    900
cgaaccttag aatgacttgt acttaccttc tttccgtaat aggatagttt ctcaggcta     960
ttaggatagt tggataaaag caatgctgca ccttttctct tcatatccta gtttgggaat   1020
tcatgccacc aaaaattgcc gctttattct ggtttaatca aagattaatg ttgtcaatag   1080
tttctcggtc gaaagagttt tctcttcata tatcctattt gaatggttac taaaatgtaa   1140
caaaaaaaaa aaaaa                                                    1155
```

<210> SEQ ID NO 6
<211> LENGTH: 236
<212> TYPE: PRT
<213> ORGANISM: Carica papaya

<400> SEQUENCE: 6

```
Met Val Val Glu Gly Thr Pro Lys Leu Leu Ser Thr Ser Val Ala Glu
1               5                   10                  15

Asp Lys Pro Asn Pro Asn Thr Ala Asn Pro Asn Ser Arg Pro Arg Gly
                20                  25                  30

Asp Glu Glu Asp Glu Gly Pro Glu Gly Glu Ile Val Asp Glu Asp
            35                  40                  45

Glu Ser Lys Arg Ser Ser Ala Val Leu Leu Gln Pro His Pro Leu Glu
        50                  55                  60

His Pro Trp Thr Phe Trp Phe Asp Asn Phe Ser Ala Lys Ser Lys Gln
65                  70                  75                  80

Ala Thr Trp Gly Ser Ser Met Arg Ser Val Tyr Thr Phe Arg Thr Val
                85                  90                  95

Glu Glu Phe Trp Ser Leu Tyr Asn Asn Ile His His Pro Ser Lys Leu
                100                 105                 110

Ala Val Gly Ala Asp Phe Tyr Cys Phe Lys His Lys Ile Glu Pro Lys
            115                 120                 125

Trp Glu Asp Pro Val Cys Ala Asn Gly Gly Lys Trp Thr Met Asn Phe
        130                 135                 140

Gln Arg Gly Lys Ser Asp Thr Cys Trp Leu Tyr Thr Leu Leu Ala Met
```

```
                145                 150                 155                 160
Ile Gly Glu Gln Phe Asp His Gly Asp Glu Ile Cys Gly Val Val
                    165                 170                 175

Asn Val Arg Gly Arg Gln Glu Lys Ile Ala Leu Trp Thr Lys Asn Ala
                180                 185                 190

Ala Asn Glu Ala Ala Gln Met Ser Ile Gly Lys Gln Trp Lys Glu Phe
                195                 200                 205

Leu Asp Tyr Asn Asp Thr Met Gly Phe Ile Phe His Glu Asp Ala Lys
    210                 215                 220

Lys Leu Glu Arg Ala Ala Lys Asn Arg Tyr Ser Val
225                 230                 235

<210> SEQ ID NO 7
<211> LENGTH: 139
<212> TYPE: PRT
<213> ORGANISM: Carica papaya

<400> SEQUENCE: 7

Met Val Val Glu Gly Thr Pro Lys Leu Leu Ser Thr Ser Val Ala Glu
1               5                   10                  15

Asp Lys Pro Asn Pro Asn Thr Ala Asn Pro Asn Ser Arg Pro Arg Gly
                20                  25                  30

Asp Glu Glu Asp Glu Gly Pro Glu Glu Gly Glu Ile Val Asp Glu Asp
            35                  40                  45

Glu Ser Lys Arg Ser Ser Ala Val Leu Leu Gln Pro His Pro Leu Glu
        50                  55                  60

His Pro Trp Thr Phe Trp Phe Asp Asn Phe Ala Lys Ser Lys Gln
65                  70                  75                  80

Ala Thr Trp Gly Ser Ser Met Arg Ser Val Tyr Thr Phe Arg Thr Val
                85                  90                  95

Glu Glu Phe Trp Ser Leu Tyr Asn Asn Ile His His Pro Ser Lys Leu
            100                 105                 110

Ala Val Gly Ala Asp Phe Tyr Cys Phe Lys His Lys Ile Glu Pro Lys
        115                 120                 125

Trp Glu Asp Pro Val Cys Ala Asn Gly Gly Lys
    130                 135

<210> SEQ ID NO 8
<211> LENGTH: 25
<212> TYPE: DNA
<213> ORGANISM: Carica papaya

<400> SEQUENCE: 8
gacataacag caattttacc cagaa                                              25

<210> SEQ ID NO 9
<211> LENGTH: 25
<212> TYPE: DNA
<213> ORGANISM: Carica papaya

<400> SEQUENCE: 9
catagtttct ttccgcttag cactc                                              25

<210> SEQ ID NO 10
<211> LENGTH: 35
<212> TYPE: DNA
<213> ORGANISM: Carica papaya

<400> SEQUENCE: 10
```

-continued cgacgttgta aaacgacggt cccctttcat gtcca                                    35

<210> SEQ ID NO 11
<211> LENGTH: 35
<212> TYPE: DNA
<213> ORGANISM: Carica papaya

<400> SEQUENCE: 11
taacaatttc acacaggtag cctttcatct ctcac                                    35

<210> SEQ ID NO 12
<211> LENGTH: 25
<212> TYPE: DNA
<213> ORGANISM: Carica papaya

<400> SEQUENCE: 12
ctctaccaca gactgtcaaa tctgc                                               25

<210> SEQ ID NO 13
<211> LENGTH: 25
<212> TYPE: DNA
<213> ORGANISM: Carica papaya

<400> SEQUENCE: 13
aggaatttcc cgaagtactg gtatc                                               25

<210> SEQ ID NO 14
<211> LENGTH: 37
<212> TYPE: DNA
<213> ORGANISM: Carica papaya

<400> SEQUENCE: 14
cgacgttgta aaacgaccct ttacaataat atacatc                                  37

<210> SEQ ID NO 15
<211> LENGTH: 34
<212> TYPE: DNA
<213> ORGANISM: Carica papaya

<400> SEQUENCE: 15
taacaatttc acacaggatg aggaacaaat aatg                                     34

<210> SEQ ID NO 16
<211> LENGTH: 24
<212> TYPE: DNA
<213> ORGANISM: Carica papaya

<400> SEQUENCE: 16
cctacccaac catggtgata agac                                                24

<210> SEQ ID NO 17
<211> LENGTH: 23
<212> TYPE: DNA
<213> ORGANISM: Carica papaya

<400> SEQUENCE: 17
gtgcagcatt gcttttatcc aac                                                 23

<210> SEQ ID NO 18
<211> LENGTH: 35
<212> TYPE: DNA
<213> ORGANISM: Carica papaya

```
<400> SEQUENCE: 18
cgacgttgta aaacgaccaa actcgtgagg catga                              35

<210> SEQ ID NO 19
<211> LENGTH: 35
<212> TYPE: DNA
<213> ORGANISM: Carica papaya

<400> SEQUENCE: 19
taacaatttc acacaggggt tcggatatga atcca                              35

<210> SEQ ID NO 20
<211> LENGTH: 5001
<212> TYPE: DNA
<213> ORGANISM: Carica papaya

<400> SEQUENCE: 20
ggagcctctg tagctaatgc atctctctcc tctaccacct ccattgctgt ttctccctct     60
ctatctccga ttttcttttt catctaattt tcagaacatt ccaatatgta cttacatatg    120
cacatacagc ttccatctct ttgatctact acatattttg tcgctaaata taaaagtaaa    180
accaatcttc tttcttgggt tccttcgtgg cagccatgca aagcgtgagg cttgaagctg    240
gcatgcggtg gaatcaccac ctgcccttac gtgagtattt tactcacgtt ttccgcttct    300
tgtgcatata aactaaggaa aataattaat ttcttgtttt tgtagaagat taattatcat    360
tcttattaat taaggtgttg tagaaatttt tttttctcg ccattaattt gaaaaattaa     420
ttattctcta ccaaatctaa tttccagtca aaaatctgac ccgacttaat ttgtgtatat    480
taaattaaaa tagtattata cgcatatatt aatatatact atttaattga aaaatatatt    540
atatataatt aagttgggtt gagatgaata atctaatgat gggcctaaat tacccaattt    600
ttggcccact aaaataaatt ccttaaaatg ggccgacaga aagctaatat agaacgttct    660
ctcctttctc actcgacagt tctgagacag aaaacacgta aacaaaagga aagcgtaatg    720
gcgagtgagg tagcgatgga ggggagcacc gtagcggcgg cggggacaac agatgcaccc    780
gttccaacag ataagcagcc ccataagctc gataagaagt ggactttctg gttcgataac    840
caatctaaga aacatggcgc cgcttggggc tcctctctcc gtaaagtttt taccttt gac    900 accgtcgaag aattctggag gtttgctacg caccctcctt ctcctcctcc tctttgtgtt    960
cataactcta tcattctgta tttatgtaat ttgtttagtg tgtatgcaat ttgatctgtt   1020
aggtacttag gttcttcttc gattttttt ttccgatctg ttcgctgctc tctattttt    1080 attcgttaat aattcctta tcttcagata tttattaaat tacatctttc tgcgttttt    1140 tttataattc cattttagta actggaactt tttaagttgg tggtatgtta atgttcttgg   1200
cattccatgt ttctttcctt tttagttgcc tggagcgtcc ttgcaaaatt aaatgcctta   1260
gggtgtcttt aaataaatga attccaccaa aaaaattgtg aatttttcgtt atagtcataa   1320 ttttttagt tagaggtgtt ctaaatatga agattttagt ttcaattaa ttttaagttg    1380 acttgaaata atgaatttca gatttattg aaattgatag aagttgaaaa ctaattatgg    1440
ccggttgaaa ggaaagcagc tatgaacata tacttcaaat acaaacagaa ttatacaata   1500
ccagtatacc accaattcac tactatgtta taaaatatct tacaaaatgg tttcttacaa   1560
aatataagaa gtcatatata aatcatttcc ttatagaatt catttgaaaa taaaataaat   1620
tttgttgttt cattttctcc aaacgtggcc ttatttctgt ttctcacatt gttatgaatc   1680
tgtaactatc atcaattgaa tgagtggttg atagtgggca ttgctcatta ttttgtctag   1740
```

```
ccatctctgg gctgattggt tgaaaaggtg cagcttaaat gtcttacttt tgttgtctac    1800
taacctgcat tctggtcatg ctttgacaag ttttcgtata ttcctcttta taaacacttc    1860
ttttgaagag aaatctaaat tagacttgct taatctaaca gggtaatctc tctttatata    1920
attgatattc tgcagtttgt acgaaaatat attcaagccc agcaagttgc tttcaaatgc    1980
tgacttccac ttgttcaaag ctggagttga gcccaaatgg gaggatcctg agtgcgctaa    2040 tgggggaaa tggactgtta tctgtagcag aaaggcaatc cttgatatca tgtggcttga     2100
aactgtaaaa ttctttacct gtctgattat tttgtttctg taaaaaatta atgtgcaaaa    2160
tgcaagttct tggtcttact tccgcgataa ctaatgtcca tttttaatga tttatgaatt    2220
ctcttcattt gggtagttga tggctttaat tggagagcaa tttgatgagg cagacgaaat    2280
ttgtggtgtg gttgctagcg tacgccagca aaggcaggac aaaatctcat gtgtgactaa    2340
gacagcagca aatgaggctg cgcaggtcta atttcttact aatttgatac ctggtactga    2400
agtttgttgt ttaatacgag cattttttta aatcctagaa gttattccaa tctgcaaagc    2460
taactcaatt ttgatcccct tgaaactgttg attttttatta gaggcaaacc tggataacta    2520
ctaggttctt cctggccttg atttgacatt ttgatatctg gaagctatat gcttgttgat    2580
ttccgaattg tagattacat gttctaatat ggtacttttg cccctccccc tactgtgcat    2640
ggaaatgctg gtgaaatttt taagagaagc aaatcctaaa gaagccattg ttgaaaattt    2700
ttataacaca ggattaaatg agaagggagc ttttgtgtga gctttagtta tgatgaaaat    2760
ttcagataaa tacaaaagga tcctacaagg gagtgactgt gtgttttgtg gttatgttga    2820
tggaaagatt tatacttacc aacttatgaa ggtcttgaac cagtttgaca tataggactc    2880
aaaacctctg ccgatgagct cttcagctgc ttttttagag ggattatgga ttttttgtttc   2940 cagggacatc taagatctca atgctataac tagtctttgt tgctttactt atccaaatag    3000
attttaccgg ttttgtttgt tgtaattttta aaactaaggg ttctaagttg tgggttgaga    3060
aagagagtgg gttatttatt tgattttag tcaccagaaa cactgacaat aaagcaatag      3120
tcttcaaatc ccccaaaaag aagattgatt tatattgaca aataatttga tgtttaaatg    3180
agtaaattga tatttcctct gttaatttgc ttgtatatca ttgctccaac tagttttggg    3240
ttgctgacat ttgggaagct aatctctatg ccagtgctat tacttctgat tccctgatgc    3300
aaatggtgtc attatattat ttatatttttc gtaaatgcac aacatcggac gccttcagta    3360
tgtctgtctc ttgcttctaa atattacctg gtacccactt gaatcctcag acatttgtat    3420
gaaccatgtt gtgcagatga gtattgggag gaaatggaag gagatcctca atatcaccga    3480
tcagatcact tacagcttcc atgtaatttt tcatttttaa gggttttgtt gattatgggt    3540
ctgttgcctc ttgctttgct tctcatattc tcattattcg gtgtatttca ggatgattct    3600
agaagggaaa gatctggaaa gcaaaaaagt cgatacaatg tgtaacctcc gggtaatttc    3660
gtgtggcaag ttgtagggag gagcaagaac ttggttgaga aggaatcaat tagctcgatt    3720
ttgtgatctg tttgccctag atgcccagat aatcaaaata tttttttgca tttaaaatga    3780
tgtttggatg taacactata atcttacaaa atcagcacat tcatagattt ttagcagttg    3840
cattatattt tatttcagcc ttttgctttt acttcactga gtcatctaaa gtcggcaact    3900
ttctacttag aactctgcat tttgctgtaa ggttgattct gaatcccatt tgtttatgag    3960
acaattcact tgtcatatat gttactcata gcttgtcagc tgttactgtt ggtattgaga    4020
gcttcccagg ctgttaaaat aatttttttag taaaatatttt tcattaaata ataatgaaag   4080
```

```
taattctaaa aagtgttatt attttgaata actgtttctt actaagtaag tattaattaa    4140
attatttgtt ttttaatctt aaaagatgca tctcttcgtt cctctcctca ttctcctcaa    4200
acttcattgt atgatgccat cttctctggt tctccagcct actactgagc atctccacca    4260
gaagatgagt tcttcgggtt ataagtactt gccatcagga ttatgggaat ctctccagcc    4320
tccataacat tttgatgcct ctcctattgg tctccttttt gctcgctatt ttacacgaag    4380
gctgtgtctt ttctagctcc actgtattat tgtcgcattg gtgatggtga agaatctatc    4440
ttttgtaact taaacacagt ttccatctct tagagacgtt gggcggtgca aaatggattt    4500
tcattacagg caacaagaca tccataggaa caccctaatc gggttagggt ttcaaggaag    4560
aagaactaaa atcagtttat gtgttttttat atgttgaaag tagattttaa ttttttgttca   4620
aataggattt ttattattta gtattttgat ctaaagtact tgacattaca aaatctgtag    4680
ctaaaaattt ggtcatctt gtccctccaa ttttctttca tttttctcgt ctacatttga    4740
gactaaattt agaacaaagt actgaattt gaattggaat tttaattttt cagattagaa    4800
ttcaaatttg aattatatat atatatatat tgtagaaatt aagatgccta aaatgaaata    4860
atatttttt aaaaaaaaat tgttgaaaaa atatttatat atgtatcatg ttttattata    4920
gaaaactaaa aattattgga aatatgtaag atagcttaga agaatagaga aacttaaaat    4980
agaaaaataa acaaattatt g                                              5001

<210> SEQ ID NO 21
<211> LENGTH: 5001
<212> TYPE: DNA
<213> ORGANISM: Carica papaya

<400> SEQUENCE: 21
ggagcctctg tagctaatgc atctctctcc tctaccacct ccattgctgt ttctccctct      60
ctatctccga ttttctttt catctaattt tcagaacatt ccaatatgta cttacatatg     120
cacatacagc ttccatctct tgatctact acatattttg tcgctaaata taaaagtaaa     180
accaatcttc tttcttgggt tccttcgtgg cagccatgca aagcgtgagg cttgaagctg     240
gcatgcggtg gaatcaccac ctgcccttac gtgagtattt tactcacgtt ttccgcttct     300
tgtgcatata aactaaggaa ataattaat ttcttgtttt tgtagaagat taattatcat     360
tcttattaat taaggtgttg tagaaatttt tttttctcg ccattaattt gaaaattaa     420
ttattctcta ccaaatctaa tttccagtca aaaatctgac ccgacttaat ttgtgtatat     480
taaattaaaa tagtattata cgcatatatt aatatatact atttaattga aaaatatatt     540
atatataatt aagttgggtt gagatgaata atctaatgat gggcctaaat tacccaattt     600
ttggcccact aaaataaatt ccttaaaatg ggccgacaga aagctaatat agaacgttct     660
ctcctttctc actcgacagt tctgagacag aaaacacgta acaaaagga aagcgtaatg     720
gcgagtgagg tagcgatgga ggggagcacc gtagcggcgg cggggacaac agatgcaccc     780
gttccaacag ataagcagcc ccataagctc gataagaagt ggactttctg gttcgataac     840
caatctaaga acatggcgc cgcttggggc tcctctctcc gtaaagtttt tacctttgac     900
accgtcgaag aattctggag gtttgctacg caccctcctt ctcctcctcc tctttgtgtt     960
cataactcta tcattctgta tttatgtaat ttgtttagtg tgtatgcaat ttgatctgtt    1020
aggtacttag gttccttctt gattttttt ttccgatctg ttcgctgctc tctattttt    1080
attcgttaat aattccttta tcttcagata tttattaaat tacatcttc tgcgtttttt    1140
ttataattc cattttagta actggaactt tttaagttgg tggtatgtta atgttcttgg    1200
```

```
cattccatgt ttctttcctt tttagttgcc tggagcgtcc ttgcaaaatt aaatgcctta    1260
gggtgtcttt aaataaatga attccaccaa aaaaattgtg aattttcgtt atagtcataa    1320 ttttttagt tagaggtgtt ctaaatatga agattttagt ttcaatttaa ttttaagttg     1380
acttgaaata atgaatttca gattttattg aaattgatag aagttgaaaa ctaattatgg    1440
ccggttgaaa ggaaagcagc tatgaacata tacttcaaat acaaacagaa ttatacaata    1500
ccagtatacc accaattcac tactatgtta taaaatatct tacaaaatgg tttcttacaa    1560
aatataagaa gtcatatata aatcatttcc ttatagaatt catttgaaaa taaaataaat    1620
tttgttgttt cattttctcc aaacgtggcc ttatttctgt ttctcacatt gttatgaatc    1680
tgtaactatc atcaattgaa tgagtggttg atagtgggca ttgctcatta ttttgtctag    1740
ccatctctgg gctgattggt tgaaaaggtg cagcttaaat gtcttacttt tgttgtctac    1800
taacctgcat tctggtcatg ctttgacaag ttttcgtata ttcctcttta taaacacttc    1860
ttttgaagag aaatctaaat tagacttgct taatctaaca gggtaatctc tctttatata    1920
attgatattc tgcagtttgt acgaaaatat attcaagccc agcaagttgc tttcaaatgc    1980
tgacttccac ttgttcaaag ctggagttga gcccaaatgg gaggatcctg agtgcgctaa    2040 tgggggaaa tggactgtta tctgtagcag aaaggcaatc cttgatatca tgtggcttga     2100
aactgtaaaa ttcttacct gtctgattat tttgttctg taaaaaatta atgtgcaaaa      2160
tgcaagttct tggtcttact tccgcgataa ctaatgtcca tttttaatga tttatgaatt    2220
ctcttcattt gggtagttga tggctttaat tggagagcaa tttgatgagg cagacgaaat    2280
ttgtggtgtg gttgctagcg tacgccagca aaggcaggac aaaatctcat tgtggactaa    2340
gacagcagca aatgaggctg cgcaggtcta atttcttact aatttgatac ctggtactga    2400
agtttgttgt ttaatacgag catttttta atcctagaa gttattccaa tctgcaaagc      2460
taactcaatt ttgatccctt gaaactgttg atttttatta gaggcaaacc tggataacta    2520
ctaggttctt cctggccttg atttgacatt ttgatatctg gaagctatat gcttgttgat    2580
ttccgaattg tagattacat gttctaatat ggtacttttg ccctccccc tactgtgcat      2640 ggaaatgctg gtgaaattt taagagaagc aaatcctaaa gaagccattg ttgaaaattt     2700
ttataacaca ggattaaatg agaagggagc ttttgtgtga gctttagtta tgatgaaaat    2760
ttcagataaa tacaaaagga tcctacaagg gagtgactgt gtgttttgtg ttatgttga    2820 tggaaagatt tatacttacc aacttatgaa ggtcttgaac cagtttgaca tataggactc    2880
aaaacctctg ccgatgagct cttcagctgc ttttttagag ggattatgga ttttgtttc     2940 cagggacatc taagatctca atgctataac tagtctttgt tgcttacttt atccaaatag    3000
attttaccgg ttttgtttgt tgtaatttta aaactaaggg ttctaagttg tgggttgaga    3060
aagagagtgg gttatttatt tgattttag tcaccagaaa cactgacaat aaagcaatag     3120
tcttcaaatc ccccaaaaag aagattgatt tatattgaca aataaatttga tgtttaaatg   3180 agtaaattga tatttcctct gttaatttgc ttgtatatca ttgctccaac tagttttggg    3240
ttgctgacat ttgggaagct aatctctatg ccagtgctat tacttctgat tccctgatgc    3300
aaatggtgtc attatattat ttatattttc gtaaatgcac aacatcggac gccttcagta    3360
tgtctgtctc ttgcttctaa atattacctg gtacccactt gaatcctcag acatttgtat    3420
gaaccatgtt gtgcagatga gtattgggag gaaatggaag gagatcctca atatcaccga   3480
tcagatcact tacagcttcc atgtaatttt tcatttttaa gggttttgtt gattatgggt    3540
```

```
ctgttgcctc ttgctttgct tctcatattc tcattattcg gtgtatttca ggatgattct    3600
agaagggaaa gatctggaaa gcaaaaaagt cgatacaatg tgtaacctcc gggtaatttc    3660
gtgtggcaag ttgtagggag gagcaagaac ttggttgaga aggaatcaat tagctcgatt    3720
ttgtgatctg tttgccctag atgcccagat aatcaaaata ttttttttgca tttaaaatga    3780 tgtttggatg taacactata atcttacaaa atcagcacat tcatagattt ttagcagttg    3840
cattatattt tatttcagcc ttttgctttt acttcactga gtcatctaaa gtcggcaact    3900
ttctacttag aactctgcat tttgctgtaa ggttgattct gaatcccatt tgtttatgag    3960
acaattcact tgtcatatat gttactcata gcttgtcagc tgttactgtt ggtattgaga    4020
gcttcccagg ctgttaaaat aattttttag taaaatattt tcattaaata ataatgaaag    4080
taattctaaa aagtgttatt attttgaata actgtttctt actaagtaag tattaattaa    4140
attatttgtt ttttaatctt aaaagatgca tctcttcgtt cctctcctca ttctcctcaa    4200
acttcattgt atgatgccat cttctctggt tctccagcct actactgagc atctccacca    4260
gaagatgagt tcttcgggtt ataagtactt gccatcagga ttatgggaat ctctccagcc    4320
tccataacat tttgatgcct ctcctattgg tctcctttttt gctcgctatt ttacacgaag    4380
gctgtgtctt ttctagctcc actgtattat tgtcgcattg gtgatggtga agaatctatc    4440
ttttgtaact taaacacagt ttccatctct tagagacgtt gggcggtgca aaatggattt    4500
tcattacagg caacaagaca tccataggaa caccctaatc gggttagggt ttcaaggaag    4560
aagaactaaa atcagtttat gtgtttttat atgttgaaag tagattttaa ttttttgttca    4620 aataggattt ttattattta gtattttgat ctaaagtact tgacattaca aaatctgtag    4680
ctaaaaattt ggtcatcttt gtccctccaa ttttctttca tttttctcgt ctacatttga    4740
gactaaattt agaacaaagt actgaatttt gaattgaat tttaattttt cagattagaa    4800
ttcaaatttg aattatatat atatatatat tgtagaaatt aagatgccta aaatgaaata    4860
atattttttt aaaaaaaaat tgttgaaaaa atatttatat atgtatcatg ttttattata    4920
gaaaactaaa aattattgga aatatgtaag atagcttaga agaatagaga aacttaaaat    4980
agaaaaataa acaaattatt g                                              5001
```

<210> SEQ ID NO 22
<211> LENGTH: 995
<212> TYPE: DNA
<213> ORGANISM: Carica papaya

<400> SEQUENCE: 22

```
gagttctgag acagaaaaca cgtaaacaaa aggaaagcgt aatggcgagt gaggtagcga     60 tggagggggag caccgtagcg gcggcgggga caacagatgc acccgttcca acagataagc    120
agccccataa gctcgataag aagtggactt tctggttcga taaccaatct aagaagcatg    180
gcgccgcttg gggctcctct ctccgtaaag ttttttacctt tgacaccgtc gaagaattct    240
ggagtttgta cgaaaatata ttcaagccca gcaagttgct ttcaaatgct gacttccact    300
tgttcaaagc tggagttgag cccaaatggg aggatcctga gtgcgctaat ggggggaaat    360
ggactgttat ctgtagcaga aaggcaatcc ttgatatcat gtggcttgaa actttgatgg    420
ctttaattgg agagcaattt gatgaggcag acgaaatttg tggtgtggtt gctagcgtac    480
gccagcaaag gcaggacaaa atctcattgt ggactaagac agcagcaaat gaggctgcgc    540
agatgagtat tggaaggaaa tggaaggaga tcctcaatat caccgatcag atcacttaca    600
gcttccatga tgattctaga agggaaagat ctggaaagca aaaaagtcga tacaatgtgt    660
```

```
aacctccggg taatttcgtg tggcaagttg tagggaggag caagaacttg gttgagaagg    720
aatcaattag ctcgattttg tgatctgttt gccctagatg cccagataat caaaatattt    780
ttttgcattt aaaatgatgt ttggatgtaa cactataatc ttacaaaatc agcacattca    840
tagattttta gcagttgcat tatattttat ttcagccttt tgcttttact tcactgagtc    900
atctaaagtc ggcaactttc tacttagaac tctgcatttt gctgtaaggt tgattctgat    960
tcccatttgt ttatgaggaa aaaaaaaaaa aaaaa                                995
```

<210> SEQ ID NO 23
<211> LENGTH: 995
<212> TYPE: DNA
<213> ORGANISM: Carica papaya

<400> SEQUENCE: 23

```
gagttctgag acagaaaaca cgtaaacaaa aggaaagcgt aatggcgagt gaggtagcga    60
tggaggggag caccgtagcg gcggcgggga caacagatgc acccgttcca acagataagc    120
agccccataa gctcgataag aagtggactt tctggttcga taaccaatct aagaagcatg    180
gcgccgcttg gggctcctct ctccgtaaag ttttttacctt tgacaccgtc gaagaattct    240
ggagtttgta cgaaaatata ttcaagccca gcaagttgct ttcaaatgct gacttccact    300
tgttcaaagc tggagttgag cccaaatggg aggatcctga gtcgctaat ggggagaaat    360 ggactgttat ctgtagcaga aaggcaatcc ttgatatcat gtggcttgaa actttgatgg    420
ctttaattgg agagcaattt gatgaggcag acgaaatttg tggtgtggtt gctagcgtac    480
gccagcaaag gcaggacaaa atctcattgt ggactaagac agcagcaaat gaggctgcgc    540
agatgagtat tggaaggaaa tggaaggaga tcctcaatat caccgatcag atcacttaca    600
gcttccatga tgattctaga agggaaagat ctggaaagca aaaaagtcga tacaatgtgt    660
aacctccggg taatttcgtg tggcaagttg tagggaggag caagaacttg gttgagaagg    720
aatcaattag ctcgattttg tgatctgttt gccctagatg cccagataat caaaatattt    780
ttttgcattt aaaatgatgt ttggatgtaa cactataatc ttacaaaatc agcacattca    840
tagattttta gcagttgcat tatattttat ttcagccttt tgcttttact tcactgagtc    900
atctaaagtc ggcaactttc tacttagaac tctgcatttt gctgtaaggt tgattctgat    960
tcccatttgt ttatgaggaa aaaaaaaaaa aaaaa                                995
```

<210> SEQ ID NO 24
<211> LENGTH: 206
<212> TYPE: PRT
<213> ORGANISM: Carica papaya

<400> SEQUENCE: 24

```
Met Ala Ser Glu Val Ala Met Glu Gly Ser Thr Val Ala Ala Gly
1               5                   10                  15

Thr Thr Asp Ala Pro Val Pro Thr Asp Lys Gln Pro His Lys Leu Asp
                20                  25                  30

Lys Lys Trp Thr Phe Trp Phe Asp Asn Gln Ser Lys Lys His Gly Ala
            35                  40                  45

Ala Trp Gly Ser Ser Leu Arg Lys Val Phe Thr Phe Asp Thr Val Glu
        50                  55                  60

Glu Phe Trp Ser Leu Tyr Glu Asn Ile Phe Lys Pro Ser Lys Leu Leu
65                  70                  75                  80

Ser Asn Ala Asp Phe His Leu Phe Lys Ala Gly Val Glu Pro Lys Trp
```

```
                      85                  90                  95
Glu Asp Pro Glu Cys Ala Asn Gly Gly Lys Trp Thr Val Ile Cys Ser
            100                 105                 110

Arg Lys Ala Ile Leu Asp Ile Met Trp Leu Glu Thr Leu Met Ala Leu
        115                 120                 125

Ile Gly Glu Gln Phe Asp Glu Ala Asp Glu Ile Cys Gly Val Val Ala
    130                 135                 140

Ser Val Arg Gln Gln Arg Gln Asp Lys Ile Ser Leu Trp Thr Lys Thr
145                 150                 155                 160

Ala Ala Asn Glu Ala Ala Gln Met Ser Ile Gly Arg Lys Trp Lys Glu
                165                 170                 175

Ile Leu Asn Ile Thr Asp Gln Ile Thr Tyr Ser Phe His Asp Asp Ser
            180                 185                 190

Arg Arg Glu Arg Ser Gly Lys Gln Lys Ser Arg Tyr Asn Val
        195                 200                 205

<210> SEQ ID NO 25
<211> LENGTH: 206
<212> TYPE: PRT
<213> ORGANISM: Carica papaya

<400> SEQUENCE: 25

Met Ala Ser Glu Val Ala Met Glu Gly Ser Thr Val Ala Ala Ala Gly
1               5                   10                  15

Thr Thr Asp Ala Pro Val Pro Thr Asp Lys Gln Pro His Lys Leu Asp
            20                  25                  30

Lys Lys Trp Thr Phe Trp Phe Asp Asn Gln Ser Lys Lys His Gly Ala
        35                  40                  45

Ala Trp Gly Ser Ser Leu Arg Lys Val Phe Thr Phe Asp Thr Val Glu
    50                  55                  60

Glu Phe Trp Ser Leu Tyr Glu Asn Ile Phe Lys Pro Ser Lys Leu Leu
65                  70                  75                  80

Ser Asn Ala Asp Phe His Leu Phe Lys Ala Gly Val Glu Pro Lys Trp
                85                  90                  95

Glu Asp Pro Glu Cys Ala Asn Gly Glu Lys Trp Thr Val Ile Cys Ser
            100                 105                 110

Arg Lys Ala Ile Leu Asp Ile Met Trp Leu Glu Thr Leu Met Ala Leu
        115                 120                 125

Ile Gly Glu Gln Phe Asp Glu Ala Asp Glu Ile Cys Gly Val Val Ala
    130                 135                 140

Ser Val Arg Gln Gln Arg Gln Asp Lys Ile Ser Leu Trp Thr Lys Thr
145                 150                 155                 160

Ala Ala Asn Glu Ala Ala Gln Met Ser Ile Gly Arg Lys Trp Lys Glu
                165                 170                 175

Ile Leu Asn Ile Thr Asp Gln Ile Thr Tyr Ser Phe His Asp Asp Ser
            180                 185                 190

Arg Arg Glu Arg Ser Gly Lys Gln Lys Ser Arg Tyr Asn Val
        195                 200                 205

<210> SEQ ID NO 26
<211> LENGTH: 25
<212> TYPE: DNA
<213> ORGANISM: Carica papaya

<400> SEQUENCE: 26
gaatcaccac ctgcccttac gtgag                                           25
```

<210> SEQ ID NO 27
<211> LENGTH: 25
<212> TYPE: DNA
<213> ORGANISM: Carica papaya

<400> SEQUENCE: 27
tactcacgtt ttccgcttct tgtgc                                    25

<210> SEQ ID NO 28
<211> LENGTH: 36
<212> TYPE: DNA
<213> ORGANISM: Carica papaya

<400> SEQUENCE: 28
cacgacgttg taaaacgact gatgggccta aattac                        36

<210> SEQ ID NO 29
<211> LENGTH: 36
<212> TYPE: DNA
<213> ORGANISM: Carica papaya

<400> SEQUENCE: 29
cacgacgttg taaaacgact atagaacgtt ctctcc                        36

<210> SEQ ID NO 30
<211> LENGTH: 25
<212> TYPE: DNA
<213> ORGANISM: Carica papaya

<400> SEQUENCE: 30
ttctccaaac gtggclttat ttctg                                    25

<210> SEQ ID NO 31
<211> LENGTH: 25
<212> TYPE: DNA
<213> ORGANISM: Carica papaya

<400> SEQUENCE: 31
atgagtggtt gatagtgggc attgc                                    25

<210> SEQ ID NO 32
<211> LENGTH: 36
<212> TYPE: DNA
<213> ORGANISM: Carica papaya

<400> SEQUENCE: 32
cacgacgttg taaaacgact ctggtcatgc tttgac                        36

<210> SEQ ID NO 33
<211> LENGTH: 36
<212> TYPE: DNA
<213> ORGANISM: Carica papaya

<400> SEQUENCE: 33
cacgacgttg taaaacgacg ttttcgtata ttcctc                        36

<210> SEQ ID NO 34
<211> LENGTH: 25
<212> TYPE: DNA
<213> ORGANISM: Carica papaya

<400> SEQUENCE: 34

```
tcaccagaaa cactgacaat aaagc                                           25

<210> SEQ ID NO 35
<211> LENGTH: 25
<212> TYPE: DNA
<213> ORGANISM: Carica papaya

<400> SEQUENCE: 35
tttgcttgta tatcattgct ccaac                                           25

<210> SEQ ID NO 36
<211> LENGTH: 36
<212> TYPE: DNA
<213> ORGANISM: Carica papaya

<400> SEQUENCE: 36
cacgacgttg taaaacgacc tgatgcaaat ggtgtc                               36

<210> SEQ ID NO 37
<211> LENGTH: 36
<212> TYPE: DNA
<213> ORGANISM: Carica papaya

<400> SEQUENCE: 37
cacgacgttg taaaacgacc gtaaatgcac aacatc                               36

<210> SEQ ID NO 38
<211> LENGTH: 37
<212> TYPE: DNA
<213> ORGANISM: Carica papaya

<400> SEQUENCE: 38
ggataacaat ttcacacagg tcaaattgca tacacac                              37

<210> SEQ ID NO 39
<211> LENGTH: 37
<212> TYPE: DNA
<213> ORGANISM: Carica papaya

<400> SEQUENCE: 39
ggataacaat ttcacacagg acctaagtac ctaacag                              37

<210> SEQ ID NO 40
<211> LENGTH: 25
<212> TYPE: DNA
<213> ORGANISM: Carica papaya

<400> SEQUENCE: 40
ggcatttaat tttgcaagga cgctc                                           25

<210> SEQ ID NO 41
<211> LENGTH: 25
<212> TYPE: DNA
<213> ORGANISM: Carica papaya

<400> SEQUENCE: 41
caaccggcca taattagttt tcaac                                           25

<210> SEQ ID NO 42
<211> LENGTH: 37
<212> TYPE: DNA
<213> ORGANISM: Carica papaya

<400> SEQUENCE: 42
```

```
ggataacaat tcacacagg cagattggaa taacttc                            37
```

<210> SEQ ID NO 43
<211> LENGTH: 37
<212> TYPE: DNA
<213> ORGANISM: Carica papaya

<400> SEQUENCE: 43

```
ggataacaat tcacacagg caggaagaac ctagtag                            37
```

<210> SEQ ID NO 44
<211> LENGTH: 25
<212> TYPE: DNA
<213> ORGANISM: Carica papaya

<400> SEQUENCE: 44

```
ccaccagcat ttccatgcac agtag                                        25
```

<210> SEQ ID NO 45
<211> LENGTH: 25
<212> TYPE: DNA
<213> ORGANISM: Carica papaya

<400> SEQUENCE: 45

```
caacaatggc ttctttagga tttgc                                        25
```

<210> SEQ ID NO 46
<211> LENGTH: 37
<212> TYPE: DNA
<213> ORGANISM: Carica papaya

<400> SEQUENCE: 46

```
ggataacaat ttcacacagg caaaatcgag ctaattg                           37
```

<210> SEQ ID NO 47
<211> LENGTH: 37
<212> TYPE: DNA
<213> ORGANISM: Carica papaya

<400> SEQUENCE: 47

```
ggataacaat ttcacacagg gcatctaggg caaacag                           37
```

<210> SEQ ID NO 48
<211> LENGTH: 25
<212> TYPE: DNA
<213> ORGANISM: Carica papaya

<400> SEQUENCE: 48

```
gttgccgact ttagatgact cagtg                                        25
```

<210> SEQ ID NO 49
<211> LENGTH: 25
<212> TYPE: DNA
<213> ORGANISM: Carica papaya

<400> SEQUENCE: 49

```
tgtctcataa acaaatggga ttcag                                        25
```